(12) United States Patent
Daniels

(10) Patent No.: US 10,597,895 B1
(45) Date of Patent: Mar. 24, 2020

(54) CITY SYSTEM

(71) Applicant: Robert Leonard Daniels, Miami, FL (US)

(72) Inventor: Robert Leonard Daniels, Miami, FL (US)

(*) Notice: Subject to any disclaimer, the term of this patent is extended or adjusted under 35 U.S.C. 154(b) by 0 days.

(21) Appl. No.: 15/587,036

(22) Filed: May 4, 2017

Related U.S. Application Data

(60) Provisional application No. 62/335,102, filed on May 12, 2016.

(51) Int. Cl.
*G06Q 10/06* (2012.01)
*E04H 5/00* (2006.01)
(Continued)

(52) U.S. Cl.
CPC ............ *E04H 14/00* (2013.01); *A01G 7/02* (2013.01); *A01G 7/045* (2013.01); *A01G 17/02* (2013.01); *A01G 22/00* (2018.02); *A01G 22/22* (2018.02); *A01G 25/00* (2013.01); *A01G 31/00* (2013.01); *A01G 33/00* (2013.01); *A01K 1/00* (2013.01); *A01K 31/00* (2013.01);
(Continued)

(58) Field of Classification Search
CPC .. E04H 1/00; E04H 5/00; E04H 1/005; E04H 14/00; G06Q 90/00; G06Q 10/08; G06Q 10/00; G06Q 10/06; B01D 46/0028; C02F 1/441; C02F 2103/002; C02F 2103/001; C12P 5/023; C12M 43/00; G05B 15/02; H02J 3/382; A01G 25/00; A01G 31/00; A01G 7/02; A01G 17/02; A01G 33/00; A01G 7/045; A01G 22/00; A01G 22/22; A01K 1/00; A01K 31/00; F24F 3/1603; F24F 2003/1657; E01B 2/00

See application file for complete search history.

(56) References Cited

U.S. PATENT DOCUMENTS 506,291 A * 10/1893 Wheeler .................. E04H 1/00
                                                        52/169.3
3,897,662 A * 8/1975 Fencl .................. E04B 1/34861
                                                        52/223.8
(Continued)

FOREIGN PATENT DOCUMENTS

CN 103106630 A 5/2013
CN 103306509 A 9/2013
(Continued)

OTHER PUBLICATIONS

"Tunnel", Wikipedia, Jan. 30, 2016 [retrieved Sep. 8, 2017]; Retrieved from the internet <URL:https://web.archive.org/web/20160130224726/https://en.wikipedia.org/wikilTunnel>.

*Primary Examiner* — Phi D A
(74) *Attorney, Agent, or Firm* — John Rizvi; John Rizvi, P.A.—The Patent Professor

(57) ABSTRACT

An ecological city system is provided including a core structure and a set of circularly arranged structures having various functions surrounding the core. A plurality of radially arranged transportation structures provide transportation between the circularly arranged structures and the core structure. The ecological city system sustains inhabitant life via a closed loop system for maximizing ecological sustainability, ecological harmony, inhabitant safety, and economic performance and efficiency.

6 Claims, 19 Drawing Sheets

(51) Int. Cl.
| | |
|---|---|
| *E04H 1/00* | (2006.01) |
| *E04H 14/00* | (2006.01) |
| *B01D 46/00* | (2006.01) |
| *C02F 1/44* | (2006.01) |
| *C02F 1/00* | (2006.01) |
| *C12P 5/02* | (2006.01) |
| *C12M 1/00* | (2006.01) |
| *G05B 15/02* | (2006.01) |
| *H02J 3/38* | (2006.01) |
| *A01G 25/00* | (2006.01) |
| *A01G 31/00* | (2018.01) |
| *A01G 7/02* | (2006.01) |
| *A01G 17/02* | (2006.01) |
| *A01G 33/00* | (2006.01) |
| *A01G 7/04* | (2006.01) |
| *A01K 1/00* | (2006.01) |
| *A01K 31/00* | (2006.01) |
| *F24F 3/16* | (2006.01) |
| *E01B 2/00* | (2006.01) |
| *A01G 22/00* | (2018.01) |
| *A01G 22/22* | (2018.01) |
| *C02F 103/00* | (2006.01) |

(52) U.S. Cl.
CPC .......... *B01D 46/0028* (2013.01); *C02F 1/004* (2013.01); *C02F 1/441* (2013.01); *C12M 43/00* (2013.01); *C12P 5/023* (2013.01); *E01B 2/00* (2013.01); *F24F 3/1603* (2013.01); *G05B 15/02* (2013.01); *H02J 3/382* (2013.01); *C02F 2103/001* (2013.01); *C02F 2103/002* (2013.01); *F24F 2003/1657* (2013.01); *G06Q 10/06* (2013.01)

(56) References Cited

U.S. PATENT DOCUMENTS

| | | | |
|---|---|---|---|
| 4,679,363 A | 7/1987 | Adams | |
| 6,470,633 B2* | 10/2002 | Showen | E04H 1/00 52/169.1 |
| 7,856,768 B2* | 12/2010 | Riley | E04H 1/00 52/169.3 |
| 2007/0233505 A1* | 10/2007 | Erb | G06Q 50/165 705/315 |
| 2014/0259997 A1* | 9/2014 | Bowling | C12M 43/00 52/173.1 |
| 2018/0274187 A1* | 9/2018 | Bardia | E04H 1/04 |

FOREIGN PATENT DOCUMENTS

| | | |
|---|---|---|
| CN | 104099840 A | 10/2014 |
| RU | 2496937 C1 | 10/2013 |

* cited by examiner

FIGURE 7.0
CENTRAL CITY CORE - ULTRA HIGH-RISE OFFICE TOWERS

FIGURE 8.0
SPECIALTY BUILDINGS

FIGURE 9.0
LARGE MODULAR MICRO-CITY
(30,000 - 90,000 POPULATION)

FIGURE 10.0
SMALL MODULAR MICRO-CITY
(20,000 - 36,000 POPULATION)

FIGURE 11.0
ECONOMY SMALL MICRO CITY

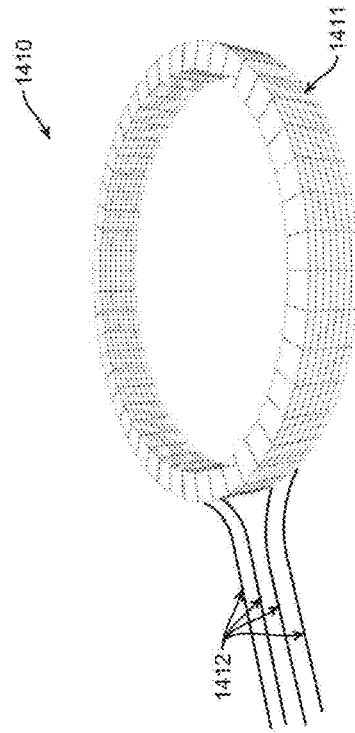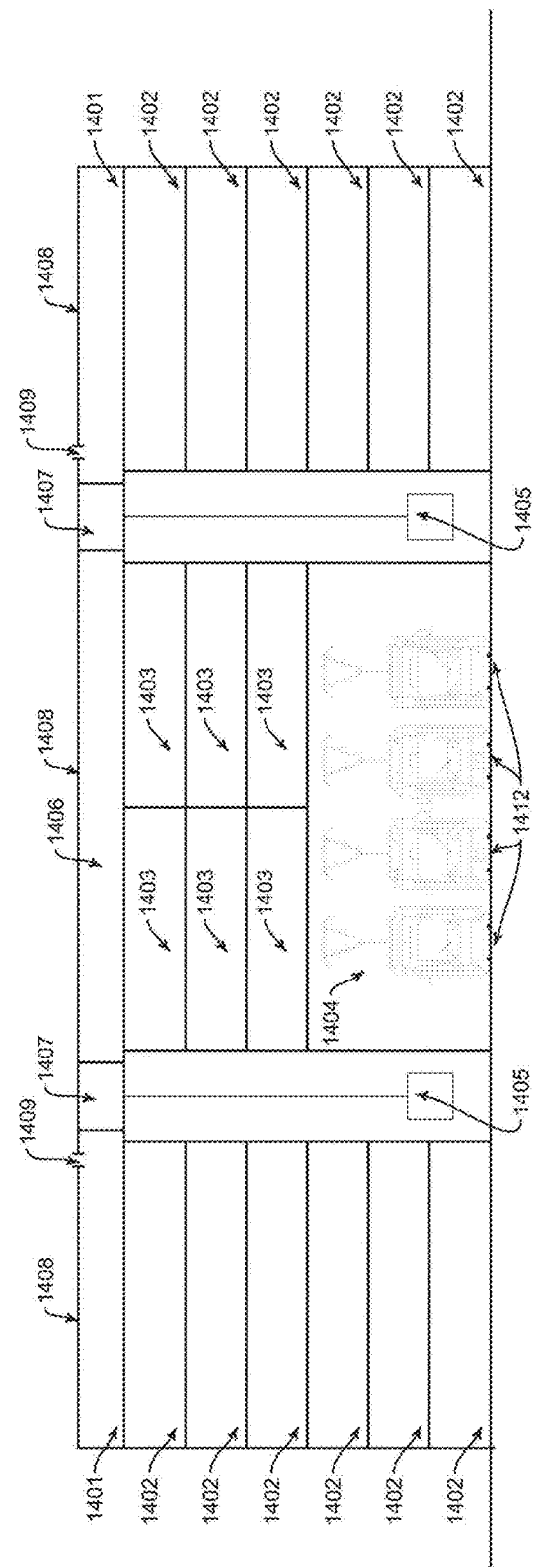

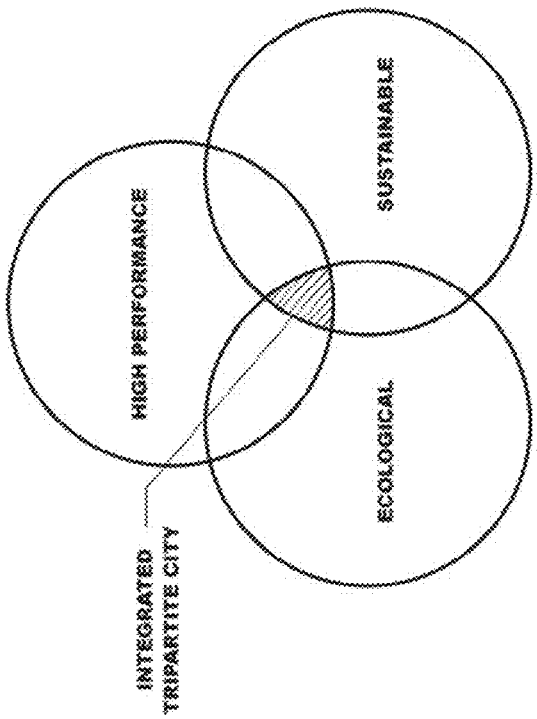

High Performance Cities — The City will have more economic efficiencies, Digitally connected "Smart Cities" for greater human interaction.
a. Digitally connected "Smart Cities" for greater human interaction.
b. Protected Transportation System to greatly reduce commute time
c. Communication & computer connectivity with fiber optics to all buildings.
d. Cyber Security enhanced by organizing cloud storage in each Micro-City
e. Cluster City has master Smart Controlled System with subset Controllers doing the majority of building control in each Micro-City.
f. City Center creates high-density interaction for over 200,000 people
g. Healthy, educated lifestyle & digital connectivity increases work output
h. This System will have greater efficiency than existing cities with Smart digital enhancements due to Infrastructure Spatial Simplification.

Sustainable Cities — The City shall protect their inhabitants from Climate Change effects, natural disasters and reduce impacts of pandemic disease.
a. Provide a constant supply of
 1. clean food
 2. clean water
 3. clean air and
 4. clean abundant energy
b. Resilient livable structure designed to withstand Climate Change and disasters.
c. To work as a unified city to have organized disaster relief for the inhabitants
d. Security system preventing unwanted human intrusion and disease intrusion
e. Air handling system will use UVc sterilizing lights to disinfect air ducts.

Ecological Cities — The City will have following characteristics to achieve ecological harmony and mitigate neg-entropic aspects.
a. Increased Bio-Diversity with over 50% dedicated space for "Wildness"
b. Elimination of heat islands and increased air flow within the city.
c. No cars, trucks and most roads; using electric mass transit = no GHG
d. Electricity produced from Renewables & nuclear = electricity w/o GHGe. Using waste heat co-generation = more electricity & no heat contamination
e. "Closed-loop" system reduces Ecological Footprint to under 0.4
f. Eliminating waste outputs by using plasma incineration or bio-remediation
g. Net Zero water/waste system will eliminate use of ground water

FIG. 15
INTEGRATE TRIPARTITE CITY

CLUSTER CITY - MASTER PROCESS PLAN

CITY SYSTEM

CROSS-REFERENCE TO RELATED APPLICATION

This application claims the benefit of U.S. Provisional Patent Application Ser. No. 62/334,102, filed May 12, 2016, which is incorporated herein in its entirety.

FIELD OF THE INVENTION

The present invention relates to the field of urban planning, and more particularly to an improved city system for facilitating ecological harmony, inhabitant safety, and economic performance and efficiency.

BACKGROUND OF THE INVENTION

The arrangement of human settlement goes back over 8,000 years. It not only involves the arrangement of buildings with connective means (roads), but also to the concept of individual land ownership. In the earliest of time, before the invention of money, large parcels of land were used as payment for favors bestowed upon associates of the ruler of the society. Those parcels were then sub-divided into smaller units again given to others in return to do some favorable action. Based upon location of the parcels and sub-parcels, houses were built and pathways (later roads) created to facilitate movement of the early village settlement. Most of these earliest sub-divisions of land occurred along meandering paths, but were later refined into square or rectangular intersections with 90 degree corners. In areas were land was not flat, but rather hilly; pathways and roads developed in level contours that facilitated movement back and forth. It must be understood that these earliest settlements were never created with an ecological understanding of the effects of human settlement concentration upon the land or flora and fauna.

The earliest settlements were small, but as human populations grew with the advent of farming, cities began to form. There was very little understanding of the function of a city. The first municipal activity was to improve the supply of water to the village. Later, the protection of a clean water supply was developed, that was not contaminated, so as to not make people sick. Eventually, it was understood that a means to eliminate human waste (urine and excrement) was necessary. Eventually the construction of durable roads was added to the assemblage that formed the design of cities. Concurrently to the development of early infrastructure was the development of building engineering to make bigger and better structures.

Design and formation of cities has not changed much for 2,000 years since the times of the Roman Empire. Many of the shapes of larger buildings and individual houses bear resemblance to those of Rome, while still maintaining city organization patterns dating back 2,500 years prior in Mehenjo-Daro in current day Pakistan.

The Twentieth Century saw the most significant changes to city development due to the common integration of new electrical energy systems powered mainly by fossil fuels, new agricultural technology spawned by oil and natural gas by-products, new transportation systems, again created from oil derivatives, and the advent of lighting and elevator technology which changed our abilities to venture vertically instead of horizontally. Yet, perhaps the greatest change to civilization and cities is the advent of the computer which drew a milestone in Mankind's ability to design new and improved structures. Further, in the last one hundred years power and communication systems were added to an increasingly complex infrastructure system that now has over 16 different sectors in the U.S. Most of these systems were never designed for increased systems loads added by a continuous population growth or the longevity requirements placed on a finitely aging system. For example, an existing sprawling city sources all food, water and fossil-fuel derived energy from outside the existing sprawling city, which are used only once and then disposed as unecological waste, causing landfill problems, solid waste issues and black water contamination of land, ground water, and lakes. Most native habitat is eliminated and destroyed with existing sprawling cities. It requires 6 times as much land with respect to an area occupied by an existing sprawling city to generate such external inputs (food, water, energy) to meet the demands of such an existing sprawling city. Being low-density, an existing sprawling city of 2 million will need about 300 square miles of land for its citizens. This city is depicted as having a physically large and ecologically unsustainable ecological footprint of about 6.0 global hectares (gha).

Development potential of existing city systems is being thwarted by archaic land ownership constraints and a very conservative approach to urban design.

Population pressures and the desire for the benefits of city life are causing the largest migration in history, of billions of people leaving the countryside and moving into the city. In the high population countries of Asia, the need for a new paradigm in urban design must occur. It is paramount to stop forcing high-density living desires into an incompatible low density infrastructure model. Rapid city-migration is in the beginning stages with over 3 billion people moving into cities during next 30 years. However, this migration will not work with the current design of newly built cities due to the present operational patterns of energy production, transportation, water and waste requirements, food availability, and clean-air requirements. An important over-looked and prevalent problem is health, sanitation and controlling the spread of contagious diseases that can sweep through a high-density city in a matter of days.

Cities are the driving force of the world economy and also the major disruptor of the Earth's environmental stability. Urban development has been focused on arranging buildings to suit the needs of people and business with little thought as to what is happening to the environment. When the human population was small, and cities were in their infancy, ecological balance was not necessary. Yet, since 1989, human consumption of Earth's extracted materials has exceeded the Earth's bio-capacity of 1.0 and climbed to 1.32. This means the Earth's capability to re-generate extracted materials is less than what humans are consuming. Humankind is increasing consumption within a finite and decreasing supply of resources.

As such, humanity is building its civilization upon a ground work of cities that is dysfunctional and flawed when confronted with the higher populations of the last 100 years. This process failure is compounded with continued dependence on primitive energy sources that are disrupting the environment and the use of transportation that was never designed to work for high-density cities.

Cities now contain over 50% of the human population and they are projected to rise to over 70% in the next 35 years. They consume 85% of all materials while occupying only 3.1% of the Earth's surface (Grimm N., Faeth S., Golubiewski N., (2008), "Global Change and the Ecology of Cities", Science, V.319, 756-760). The current system rewards the single use of materials for convenience while creating a huge waste flow that is ultimately returned back to Nature in a most economically expeditious manner. This huge imbalance of consumption and waste is stressing the environment beyond healthy limits. Without improving city-systems, a very dramatic and quick demise will occur. At a tipping point (i.e. known as Abrupt Climate Change according to the Committee of Abrupt Climate Change) the Earth's ecosystems may quickly cascade to an extreme, irreversible and disastrous situation, threatening all lifeforms as they are known.

Groundwater, clean drinking water existing in underground aquifers under the surface of the Earth for hundreds of thousands of years, is one of the Earth's most precious assets. It is squandered most flagrantly by those that have it and desired most fervently by those who need it.

As we destroy the oceans and cut down forests, the generators of oxygen (blue-green algae) are decimated as well. Within a matter of one hundred years oxygen levels may drop from 20% to 10% with resultant anoxia similar to what has occurred during other great extinction events. This will all occur if humanity continues to release Greenhouse Gas into the atmosphere, destroy more natural habitat and pollute the oceans (Warner M., Fu F., Zhang Y., (2007), "Effects of Increased Temperature & $CO_2$ on Photosynthesis, Growth 8 Elemental Ratios in Marine Synechococcus and Prochlorococcus (Cyanobacteria)", *J. Phycology*, V.43, 485-496).

Climate change is a word used to generally describe the cumulative effects of the disruptive forces of mankind. However, one of the main causes of the Earth's destabilization or ecosystem disruption is the destruction of the natural habitat of billions of creatures who were displaced by farms and cities. The farms have depleted the soils of natural nutrients and now use excessive amounts of fertilizers and pesticides in order to grow crops. They use excessive amounts of water (due to irrigation inefficiency) to produce the crops with over 50 gallons to produce a pound of edible cereal grain. The meat, dairy and poultry industries produce food through an even more inefficient process of taking feed grown elsewhere and giving it to the animals. It takes over 1,847 gallons of water to produce one pound of beef and 582 gallons of water to produce a pound of chicken. The chemicals used in animal production are flushed into the groundwater at feedlots where the animals are raised. Urine and manure waste travels through the ground, into ground water, rivers, lakes and end up meeting the ocean at estuaries. There, nitrogenous contaminants react with algae causing blooms that de-oxygenate the water, killing sea life. While 74% of the planet is covered with water, only 1.5% of this water is usable as uncontaminated drinking water. Yet in many countries, we flush our toilets, wash our clothes and water our lawns with quality water that is being wasted.

Climate change is chiefly caused by the burning of fossil fuels that produce $CO_2$, $CH_4$, $SO_2$, $NO_2$, arsenic, and mercury. The largest perpetrator of pollutants are coal fired electric plants, as the coal used is not pure and contains many contaminants that are combusted during the heating process. Coal powered electrical generation accounts for 50% of all $CO_2$ generation; with 75% of that used in electric and heat generation, as well as 25% used in manufacturing. Refined oil (gasoline) accounts for another 25% of $CO_2$, and fuel oil for heating another 5% of $CO_2$ generation. Natural gas releases about 15% of all $CO_2$, used for electric generation and heating in houses. A secondary effect of $CO_2$ generation is the interaction of atmospheric $CO_2$ with the surface of the oceans. There is a chemical reaction that occurs causing $CO_2$ to be converted in $H_2CO_3$ carbonic acid. This is causing great damage to the oceans resulting in ocean acidification that is decalcifying much of the marine life, including severe damage to coral around the world. As such, climate change and imbalances caused by human activity is permanently affecting wildlife diversity and animal and human welfare.

Another action that accentuates climate change (global warming) is the way humans are currently building their cities with continuous hard, heat absorbing surfaces (asphalt roads and concrete buildings) resulting in a phenomenon called "Heat Islands". This can increase heat by 4-5 degrees C. in the center of the city. These structures absorb heat rather than reflecting it or converting solar energy into organic matter from photosynthesis.

Most of the climate change issues that are arising have occurred within the last 60 years. Our awareness of these issues has only come to full fruition within the last 40 years. Unfortunately, both urban planners and architects have yet to integrate urban ecology into their realms to create a viable solution that works with nature as well as people.

Various agreements and conferences have been arranged between political entities to agree upon international regulations for addressing climate change. However, such arrangements usually result in a status quo and no subsequent useful change.

Various systems exist that attempt to address some of the concerns above. However, these current systems unfortunately rely on the use of standard infrastructure such as roads, combustion engine cars, and delivery trucks for transportation (obtaining only 20.8% energy utilization efficiency according to the Lawrence Livermore National Laboratory), and an electric grid with long distance electrical transport. Such currently existing long distance electrical transport systems merely have about 33% efficiency, resulting in a 67% loss. Existing systems further neglect the ecologically sustainable production and consumption of resources such as energy, food, and clean water, neglect global wildlife diversity or human welfare, or are focused on small-scale housing of inhabitants. The existing systems further neglect disease prevention for inhabitants.

Accordingly, there is an established need for a realistic solution for humans to live in harmony with nature.

SUMMARY OF THE INVENTION

Disclosed is an ecological city system, comprising, central core structures, a plurality of circularly arranged structures surrounding the core, the structures including a set micro-cities, a factory structure, a farm structure, and a transportation structure, a plurality of radial transportation structures configured to provide transportation between the circularly arranged structures; and the circularly arranged structures being configured to function as a closed loop system for maximizing ecological sustainability, ecological harmony, inhabitant safety, and economic performance and efficiency.

In another aspect, the transportation structure is a corridor including multiple levels of bi-directional traffic, each level being dedicated to a mode of transport.

In another aspect, the transportation structure includes a pedestrian level, a rail level, an autonomous car level, and a pedestrian powered vehicle level.

In another aspect, the transportation structure is both above and below ground.

In another aspect, the farm structure produces and processes food for being delivered to a micro-city of the set of micro-cities.

In another aspect, the farm structure includes waste processing equipment for processing waste.

In another aspect, the waste processing equipment is configured to process the waste via anaerobic digestion.

In another aspect, the factory structure includes a freight loading area for loading freight to be transported.

As another embodiment, disclosed is an ecological city system, the system comprising, at least one micro-city ring surrounding a central core building arrangement, the ring including a plurality of micro-cities, at least one radial transportation corridor radially configured for providing transportation between at least one micro-city of the micro-city ring and the central core building arrangement, and at least one non-radial transportation corridor configured for providing transportation between at least one micro-city of the micro-city ring and another micro-city of the micro-city ring.

In another aspect, at least one of the transportation corridors is configured for two-way transportation.

In another aspect, the micro-city ring is concentrically arranged to surround the central core building arrangement such that the micro-city ring is radially separated from the central core building arrangement.

In another aspect, the system further comprises at least one factory ring and at least one farm ring.

In another aspect, the system further comprises at least one factory ring and at least one farm ring, where the factory ring includes at least a freight loading area and a train system for transporting freight through the factory ring, and where the farm ring includes at least multiple levels and is configured to collect rainwater, grow plants, process and package food, receive and anaerobically digest organic waste, extract methane from the organic waste, aerobically digest the waste via applying enzymes, dry and grind the waste, sanitize the waste via applying heat and ultraviolet light to the waste to form dry matter, and at least one of provide the dry matter as feed for animal production and disperse the dry matter on landscape as mulch.

In another aspect, the system further comprises at least one specialty building ring, the specialty building ring including at least one of a government building, graduate university, undergraduate university, senior care center, recreation structure, shopping galleria, hotel, performing arts center, and museums.

In another aspect, the central core buildings arrangement includes residence and office buildings and a central transportation hub.

In another aspect, at least one of the transportation corridors includes a roadway layer configured to allow transportation via autonomous vehicles, a mass transit layer, a pedestrian and human powered vehicle layer, a crawl space for allowing wildlife to laterally pass through the at least one transportation corridor, an underground pedestrian tunnel, and a subway.

A process for sustaining an ecological city system, the method comprising, receiving air at a filter, sterilizing the air via ultraviolet sterilization to form sterilized air, passing the sterilized air through a building for human consumption, receiving carbon dioxide from the building, providing the carbon dioxide to a farm, receiving waste from the building, converting the waste to energy via anaerobic digestion, grinding, composting, and drying remaining waste and providing the remaining waste to the farm as mulch, at the farm, receiving and filtering rain via reverse osmosis to form filtered water, and providing the filtered water to the building for human use, receiving at the building, organic food matter from the farm, and producing electricity for the building.

In another aspect, the process further comprises, receiving oxygen from the farm, subsequent to anaerobic digestion of the waste, processing the waste via bio-remediation, plasma incineration, and accelerated decomposition, subsequent to the decomposition, extracting water from the waste via filtration, at the farm, recycling water and water vapor within the farm, and receiving greywater from the building and applying filtration to the greywater.

In another aspect, the electricity is produced via at least one of solar, wind, and nuclear power generators.

In another aspect, converting the waste to energy includes extracting methane from the waste.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 14 shows a sectional view of a factory ring, the section taken along sectional line 14-14 of FIG. 2, in accordance with the present disclosure;

FIG. 14A shows a perspective view of a factory ring, in accordance with the present disclosure;

FIG. 15 shows a chart describing an integrated tripartite city, in accordance with the present disclosure;

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
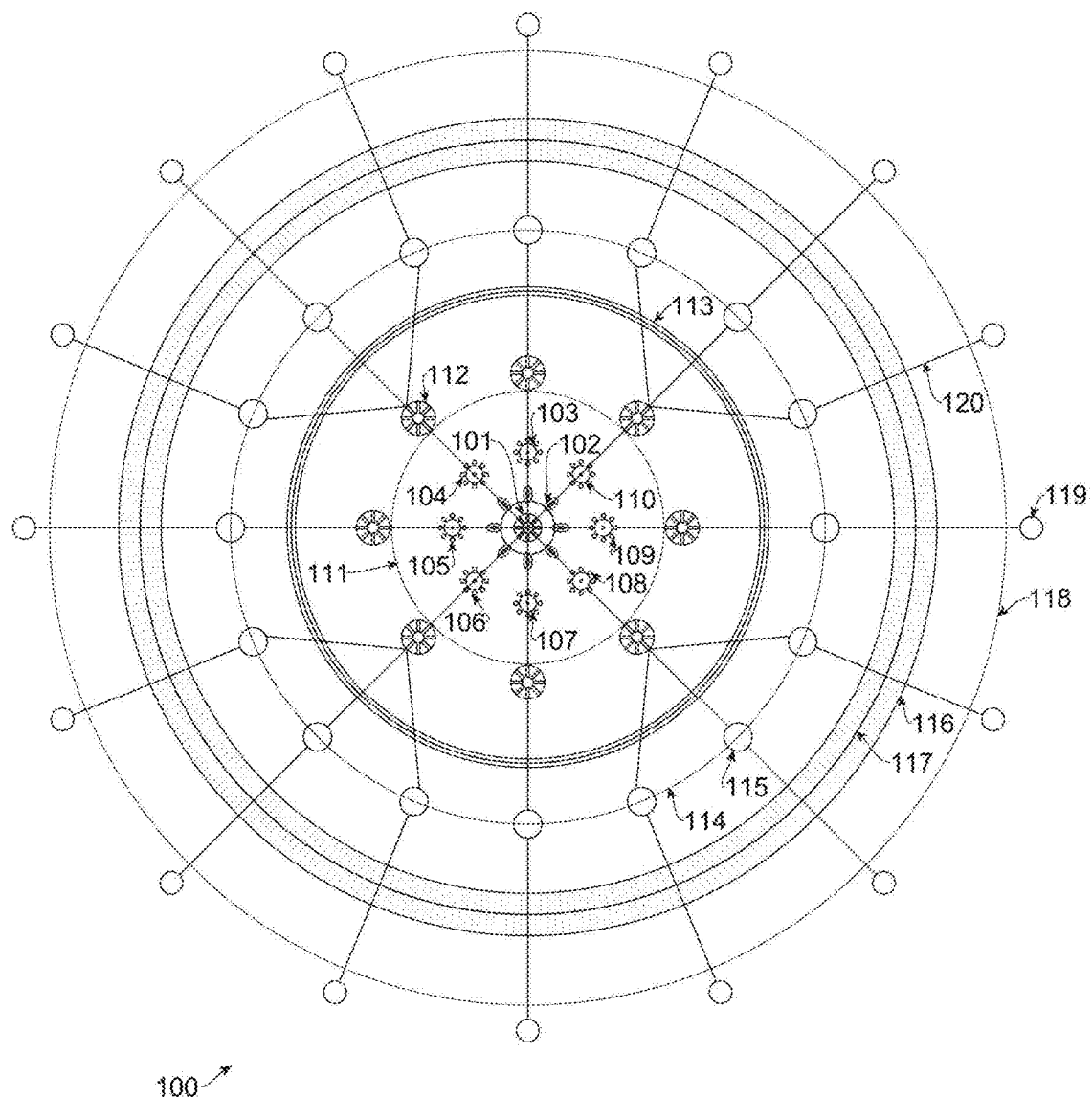
FIG. 1 shows a typical mixed-use, modular city with a work force divided by office, factory and agriculture sectors, in accordance with the present disclosure.

The illustration of FIG. 1 shows a plan view of a typical mixed-use, modular city with a work force divided by office, factory and agriculture sectors. Its final population is between 1.0-2.5 million people. The disclosed series of Micro-Cities are each semi self-contained such that there is sufficient mixed-use activities within each Micro-City, and such that each Micro-City could be defined as a district or town. The Micro-Cities may be built on a flat plain or hill that has sonic or no significant changes in elevation. The Cluster City 100 depicted in FIG. 1 is an entire assemblage of structures (Micro-Cities, Factory Rings, Vertical Farm Rings, Transportation Corridors, Specialty Buildings) that may vary in ground elevation, and that includes Central Core office buildings 101 and Central Core residence towers 102 both located within a circular pattern or arrangement, shown in FIG. 1 including 8 units but could include any quantity.

There is a circular row (arrangement) of structures outside the residence towers (on an opposite side relative to the core, the circularly arranged row being between the core and the residence towers) that is a series of Specialty Buildings, a government building 103, a Graduate University 104, an Undergraduate University 105, a Senior Care Center 106, a complete Surgical Hospital 107, a Recreation/Amusement structure 108 (e.g. an arena), a shopping galleria or 5-star hotel 109, a Performing Arts Center and museum 110. Further out is a circularly arranged two-way transportation corridor 111 that stops at each Micro-City 112. Outside this circularly arranged pattern is a low-rise cylindrical Factory Ring 113 (arrangement) where all manufacturing and industry occurs. There is a full heavy duty two-way freight train system in the middle of the Factory Ring 113 extending along the factory ring 113. This structure will employ over 50% of the workforce, all within walking distance of other important (e.g. life sustaining) structures such as residential units/towers. Outside the Factory Ring (arrangement) is a circular row (arrangement) of either large or small Micro-Cities 115, connected by another two-way transportation corridor 114 (circular arrangement). Further outside of this row of Micro-Cities is a large cylindrical structure (circular arrangement) containing a Vertical Farm 116 and a waste conversion operation. In the center of this structure is a two-way conveyance system 117, carrying food materials radially to other parts of the City. Further outside of the Farm Ring is another series of circularly placed (ring, or circular arrangement) small Micro-Cities 119, with an adjacent (outer) circularly arranged two-way transportation corridor 118 adjacent the circularly arranged ring of Micro-Cities 119. In addition to the circularly arranged transportation system is a series of radial two-way transportation corridors 120, forming spokes that will bring citizens from the inner areas to the outer areas. For example, the transportation spokes may run between various rings or circularly arranged cities or structures (e.g. the spokes may transport citizens between and to any structure or ring of structures, the ring of structures disposed between a core of a circularly arranged Cluster City and a distal (outer) point on a circumference or perimeter of the Cluster-City. It is to be understood that the term "outer" or "outside" refers to regions disposed in a radial direction away from a reference point (e.g. a point on a ring) to a distal point of a circularly arranged Cluster-City. Similarly "outward" refers to a direction radially away from a core or center of a ring. For example, an outer area of circularly arranged Micro-Cities is an area disposed radially outside the ring and away from the core. For example, the circularly arranged Vertical Farm 116 is outside of the circularly arranged row or ring of Micro-Cities 115 as shown in FIG. 1. The term "inward" has an opposite meaning to "outward" as used herein. For example, "inside" means being directed radially toward the core or center, and outside may mean being directed radially away from the core or center. Further, it is to be understood that the herein disclosed rings may be described as having a non-radial arrangement. For example, the rings may extend laterally with respect to a longitudinal, radial element such as the herein disclosed radial transportation corridors.

Figure 2:
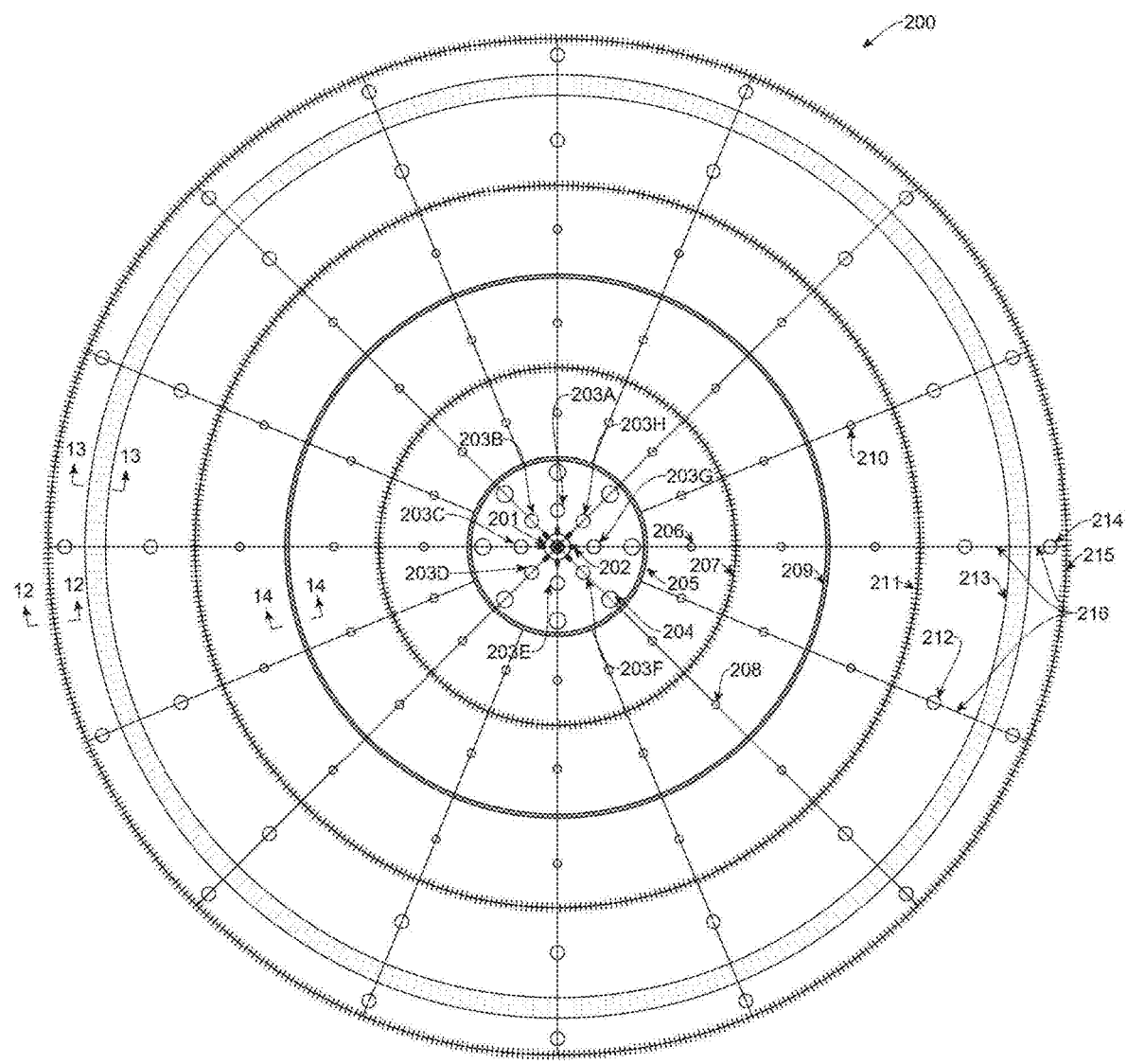
FIG. 2 shows a plan view of a factory city including two factory rings, in accordance with the present disclosure.

The illustration of FIG. 2 shows a plan view of a Factory City 200 with two circularly arranged Factory Rings, instead of one. This allows more workers to reside within walking distance of the factories. This circularly arranged factory city is capable of holding over 2,000,000 people. The Central City Core (in the center of the factory city 200), includes a series of ultra-high-rise office towers 201, with a circularly arranged row of high-rise residential towers 202 just outside them. There is a circularly arranged row outside the Residences that is a series of Specialty Buildings, a government building 203A, a Graduate University 203B, an Undergraduate University 203C, a Senior Care Center 203D, a complete Surgical Hospital 203E, a Recreation/ Amusement structure 203F (e.g. an arena), a shopping galleria or 5-star hotel 203G, a Performing Arts Center and meeting rooms 203H. Just outside the ring of circularly arranged specialty buildings is a row of circularly arranged large Micro-Cities 204. Just outside the ring of circularly arranged Micro-Cities 205 is a first of two circularly arranged Factory Rings 205. Just outside the factory ring is another ring of micro cities 206. Just outside the ring of micro cities 206 is a two-way transportation corridor 207 (ring). Outside of this is another row of circularly arranged small Micro-Cities 208. Beyond (outside) this row (ring) 208 is a second Factory Ring 209. Outside of this Factory Ring is another circularly arranged row of circularly arranged small Micro-Cities 210. Just outside the row of micro cities 210 is another circularly arranged two-way transportation corridor 211. Just outside the circularly arranged two-way transportation corridor 211 is another circularly arranged row of small Micro-Cities 212. Lastly, is the circularly arranged Vertical Farm Building 213 (ring) with the last row of small Micro-Cities 214 outside of the Vertical Farm and the last two-way Transportation Corridor 215 servicing this outer row 214. To complement the circularly arranged transportation corridors are a series of radial Spoke Transportation Corridors 216 that traverse to the center between outer distal points of the cluster factory city 200.

Figure 3:
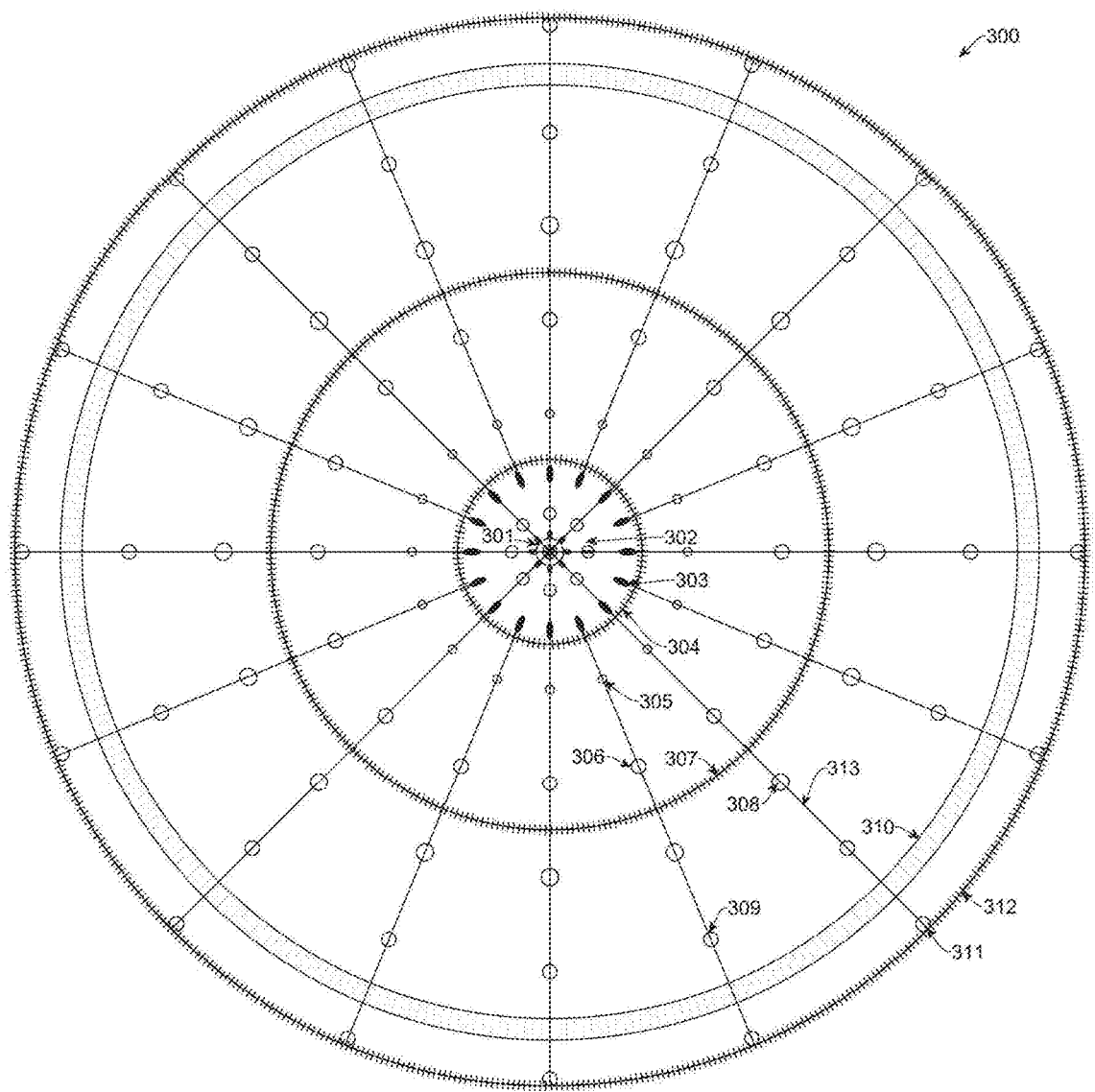
FIG. 3 shows a plan view of a professional city, in accordance with the present disclosure.

The illustration of FIG. 3 shows a plan view of an office/financial/government/capital professional city 300 that includes no factories and factory ring. If repairs are needed, small workshops within the circularly arranged Micro-Cities will be able to effect those repairs. This City includes an enlarged Central City Core with two circularly arranged rows of Office Buildings to increase the quantity of available office space in this Cluster City. The Central City Core 301 is made up of a center cluster of ultra-high rise office buildings and an outer circularly arranged row of high-rise residential towers. Further out is a circularly arranged row of Specialty Buildings 302, such as government buildings, universities, hospitals, senior care facilities, amusement and recreation facilities, and a galleria shopping center with a hotel. Outside of this is the second circularly arranged row of office towers 303. Just outside the office towers is a two-way Transportation Corridor 304. Further out is a circularly arranged row of Small Micro-Cities 305, then another row of Small Micro-Cities 306 then another two-way Transportation Corridor 307, the row of small Micro-Cities 306 being just outside row 305, and the two-way Transportation Corridor 307 being just outside row 306. Outside the Transportation Corridor is a circularly arranged row of Large Micro-Cities 308, followed by another row of small Micro-Cities 309. Just outside the small micro cities 309 (ring) is a cylindrical ring Vertical Farm 310. Just outside the Vertical Farm row 310 is another row of Micro-Cities 311 and outside the row of Micro-Cities 311 is a most outer Transportation Corridor 312 (ring).

Figure 4A:
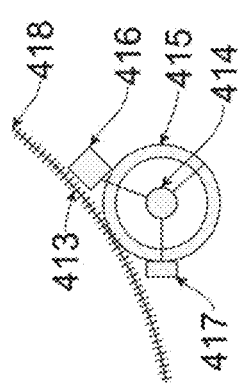
FIG. 4A shows a plan view of a typical small farming village of about 15,000 people or more, in accordance with the present disclosure.
Figure 4B:
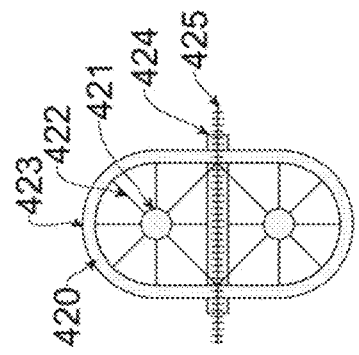
FIG. 4B shows a plan view of a mining town of about 20,000-100,000 people, in accordance with the present disclosure.
Figure 4C:
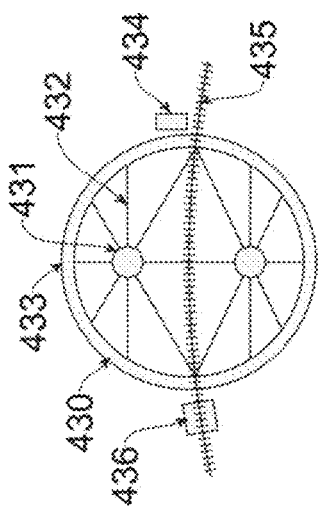
FIG. 4C shows a plan view of a larger farming town of 30,000-100,000 people, in accordance with the present disclosure.
Figure 4:
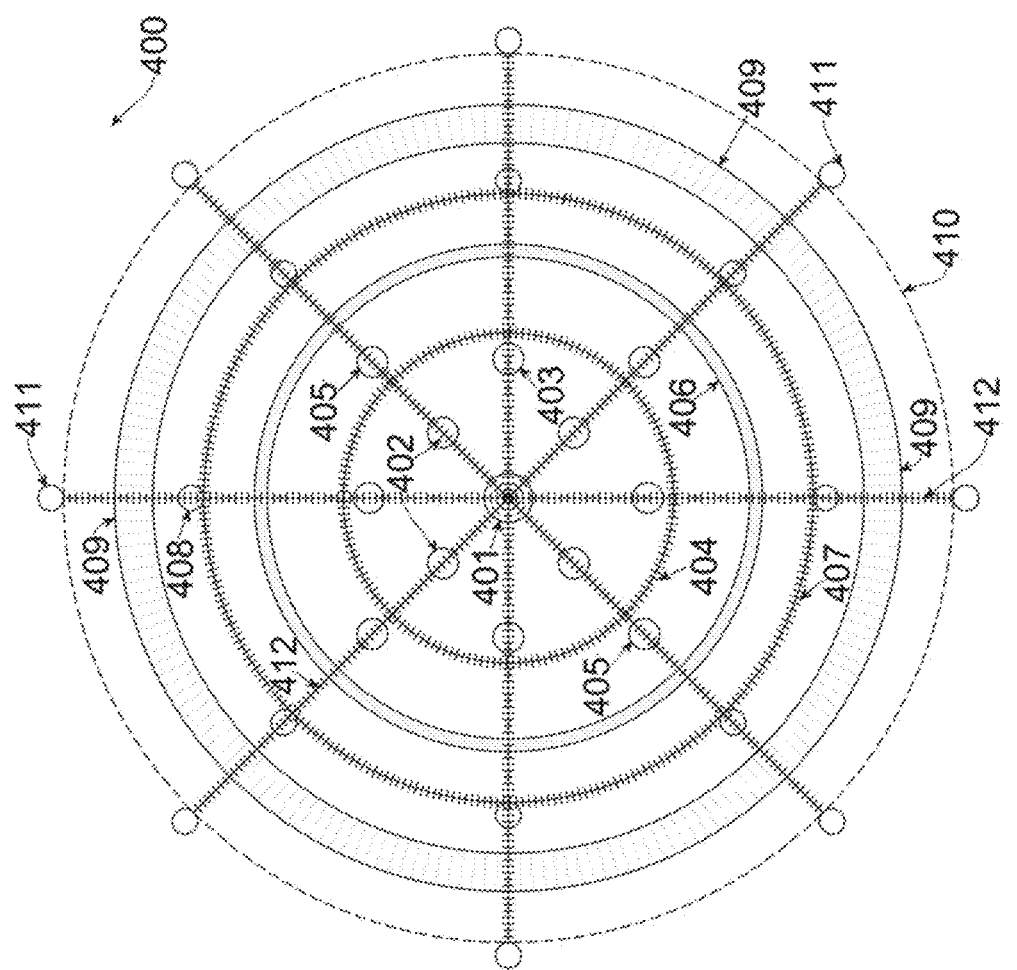
FIG. 4 shows a plan view of a smaller city of about 500,000 people with subsequent expansion, in accordance with the present disclosure.

The illustration of FIG. 4 shows a smaller city of about 500,000 people 400. The largest area of migratory growth in most of the Developing World will be to cities of 300,000 to 600,000 people. We have designed such a city with limited quantity of Micro-Cities. There is even space designed for expansion of the outer row. The Central City Core 401 is comprised of individual office and residential towers in close circularly arranged formation. Outside of this are 4—Specialty Buildings 402 that house government buildings, hospitals, university facilities, recreation/amusement facilities and galleria shopping centers with a major hotel. Next (outside) is a ring of 4—Small Micro-Cities 403, a two-way Transportation Corridor 404 (ring) then a circularly arranged row of Large Micro-Cities 405 outside of this ring 404. A single Factory Ring 406 occurs outside the ring 404, followed by another two-way Transportation Corridor 407 (ring) followed by (outside) another row of large Micro-Cities 408. Lastly is the cylindrical Vertical Farm 409 ring as an outer ring. There is an expansion area to the outside of the Vertical Farm ring where an additional row of Micro-Cities 411 can be built and connected to radial extensions of the two-way Transportation Corridor 412 also with the capability to create another circularly arranged two-way Transportation Corridor 410 (shown in dashed line).

The illustration of FIG. 4A shows a suggested plan view of a typical small Farming Village 413 of 15,000 people or more, mixed-use, modular city with a small Micro-City 414 in the center with work force divided by office, limited factory and mostly agriculture sectors. A small diameter Cylindrical Vertical Farm 415 supplies food all year for inhabitants. Other buildings include a small equipment repair factory 417 and a food processing plant 416 that is next to a connecting rail line 418 that transports food and people back to larger populated regional areas. Covered Walkways 416 connect the central city to the other buildings.

The illustration of FIG. 4B shows a suggested plan view of Mining Town 420 of about 30,000-100,000 people living in an isolated area. The town includes 2—Micro-Cities 421 with Covered Walkways 422 connecting the central cities to the ovular shaped Vertical Farm 423 and the ore processing plant 424 located in the middle next to a main rail line 425 that carries ore and people to regional centers.

The illustration of FIG. 4C shows a suggested plan for a larger farming town 430 of 30,000-100,000 people with 2—central Micro-Cities 431, with connecting Covered Walkways 432 radiating outward to both the cylindrical Vertical Farm 433 and the Equipment Repair Facility 434, the connecting rail line 435 and the food processing plant 436.

Figure 5:
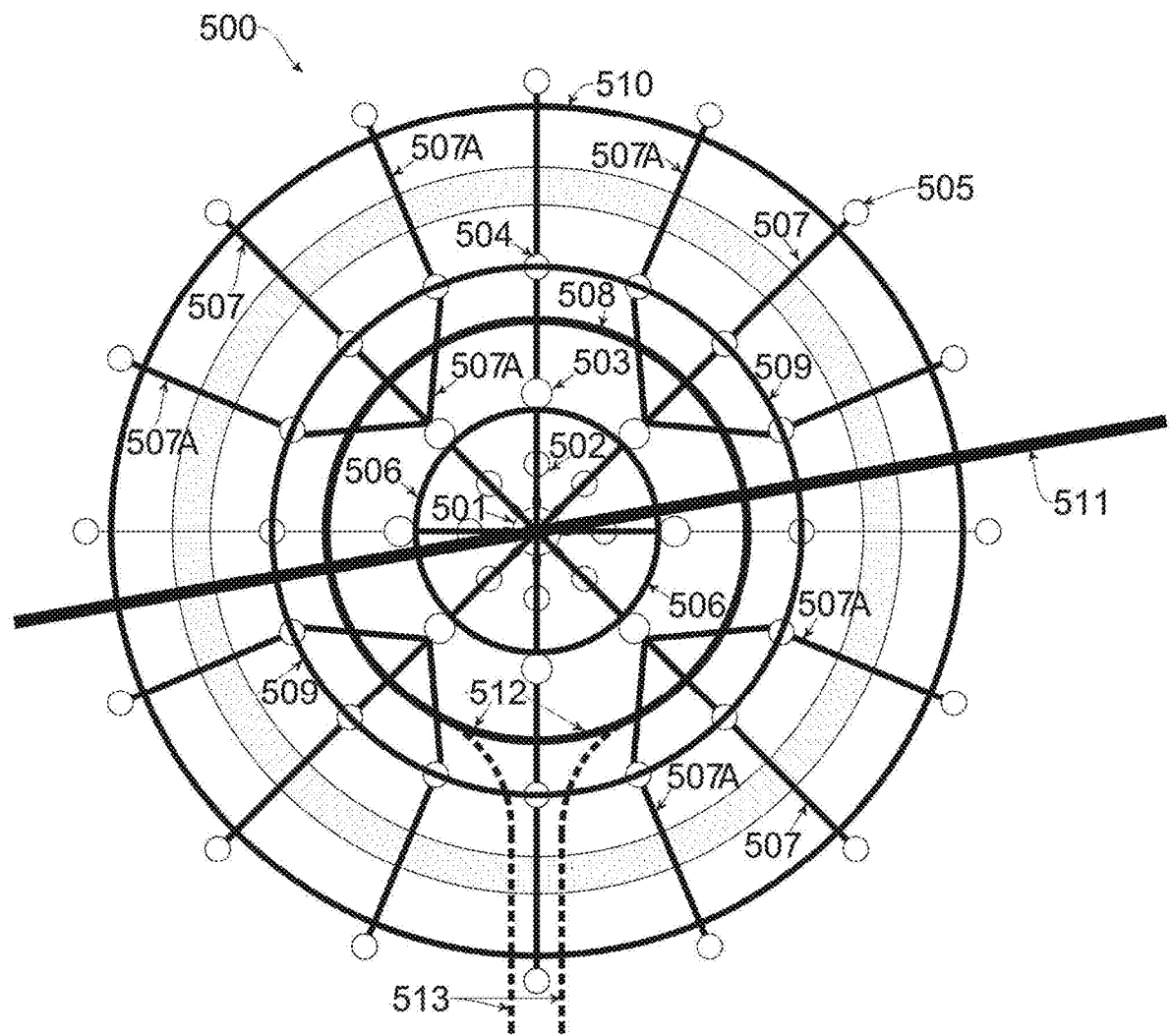
FIG. 5 shows a plan view of a transportation plan for a typical cluster city, in accordance with the present disclosure.
Figure 6:
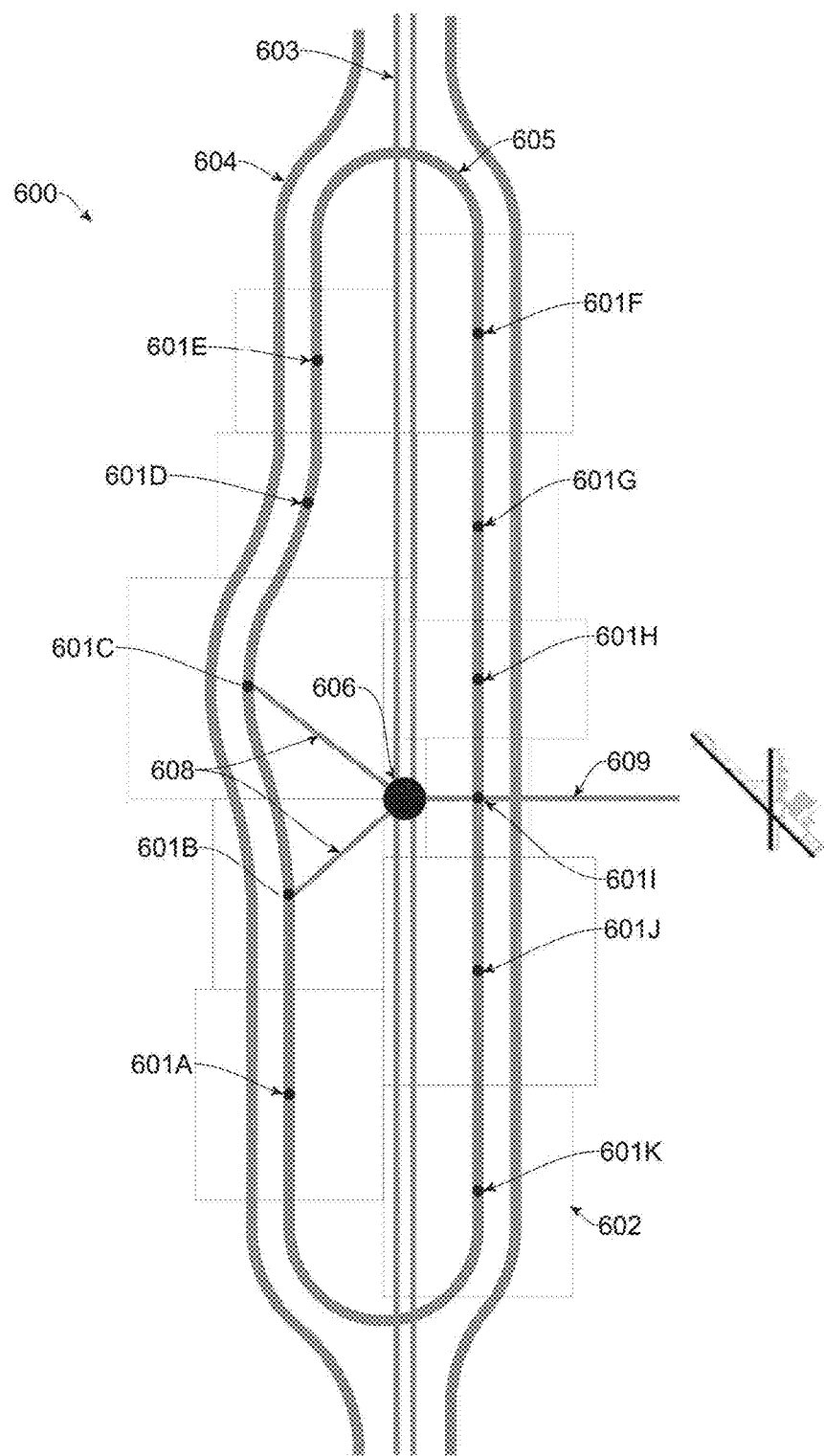
FIG. 6 shows a plan view of a regional mega-city development plan for over 25 million people, in accordance with the present disclosure.

The illustration of FIG. 5 shows a transportation plan 500 for a typical Cluster City with a Central City Core 501 that contains the Central Transportation Hub, including a Mag-Lev train 511 stop that would connect this Cluster City to adjacent Cluster Cities that are a part of Regional Mega-City (see FIG. 6). Outside the Central City Core are the Specialty Buildings 502 that are radially located along Radial-Spoked Transportation Corridors 507 that transport people from the center of the City to the extreme outer ring of Micro-Cities 505. There are three (3)—circularly arranged Transportation Corridors depicted in this City that includes the Inner Transportation Corridor 506 connecting inner row of Micro-Cities 503, the middle row of Micro-Cities 504, Middle circularly arranged Transportation Corridor 509 and the Outer Transportation Corridor 510. The Factory Ring 508 includes a heavy-duty freight train rail in the middle of the building. This freight line 512 is two-way and ultimately exits the city and connects to the Regional Freight System at 513.

The illustration of FIG. 6 shows a Regional Mega-City Development Plan 600 that includes multiple Cluster Cities 601A through 601K of varying sizes and functions. This Regional City can reach populations of over 25 million people. The boundary of each Cluster City 602 defines their limits of growth. Through the middle of the Regional Mega-City runs a high-speed train 603, with a Central Transportation Hub 606. Subway trains 608 connect the Central Transportation Hub 606 to the Mag-Lev Train 605. Subway train 609 connects the hub to the Regional Airport 607. The Regional Freight Line 604 connects to the Factory Ring Freight lines in each Cluster City for transporting freight.

Figure 7:
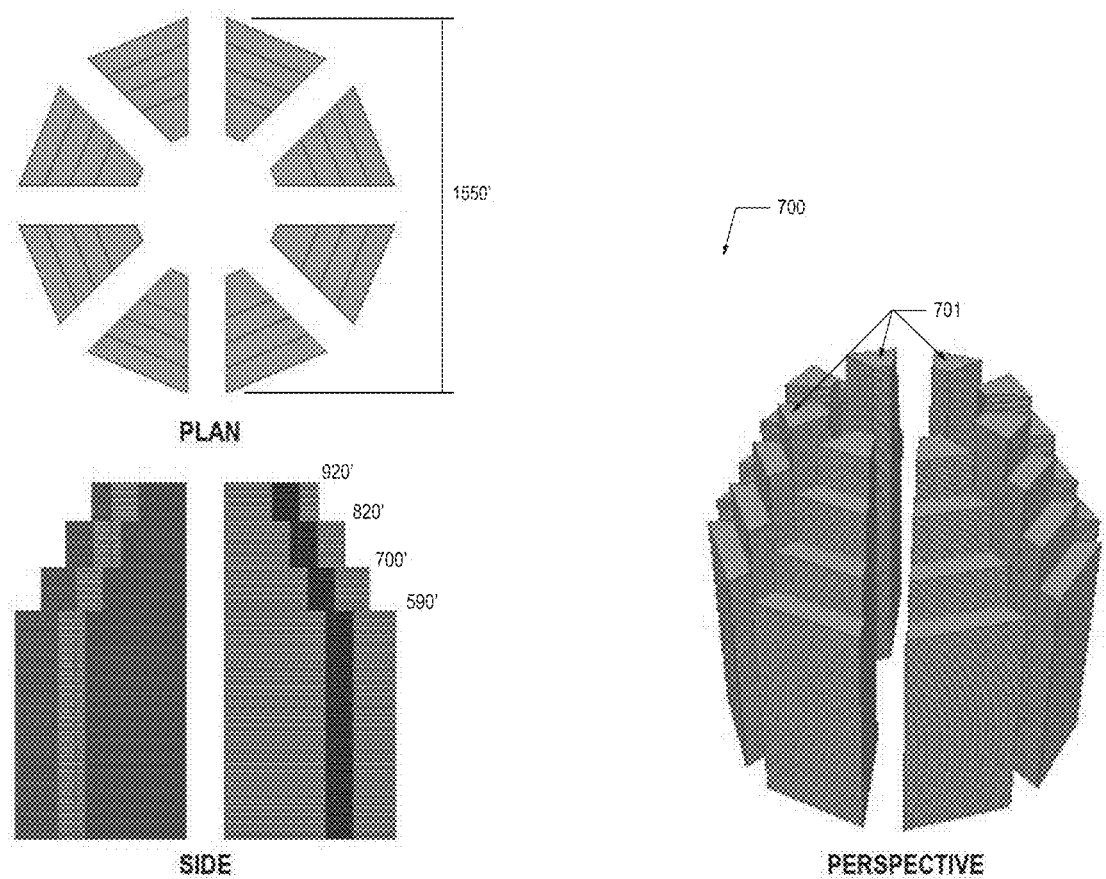
FIG. 7 shows a plan, side, and perspective view of a central city core of an ultra-high rise office tower complex, in accordance with the present disclosure.

The illustration of FIG. 7 shows an example of the Central City Core 700 which is comprised of multiple Ultra High-Rise Towers 701 that will create an extremely high-density corporate work environment. The concentration of professional workers in close proximity has great value according to experts in Urban Economics. The buildings may be of equal or different height. The buildings may be of duplicate shape for uniformity or may be different shapes and create an asymmetric pattern. The structure occurs below ground as well as above.

Figure 8:
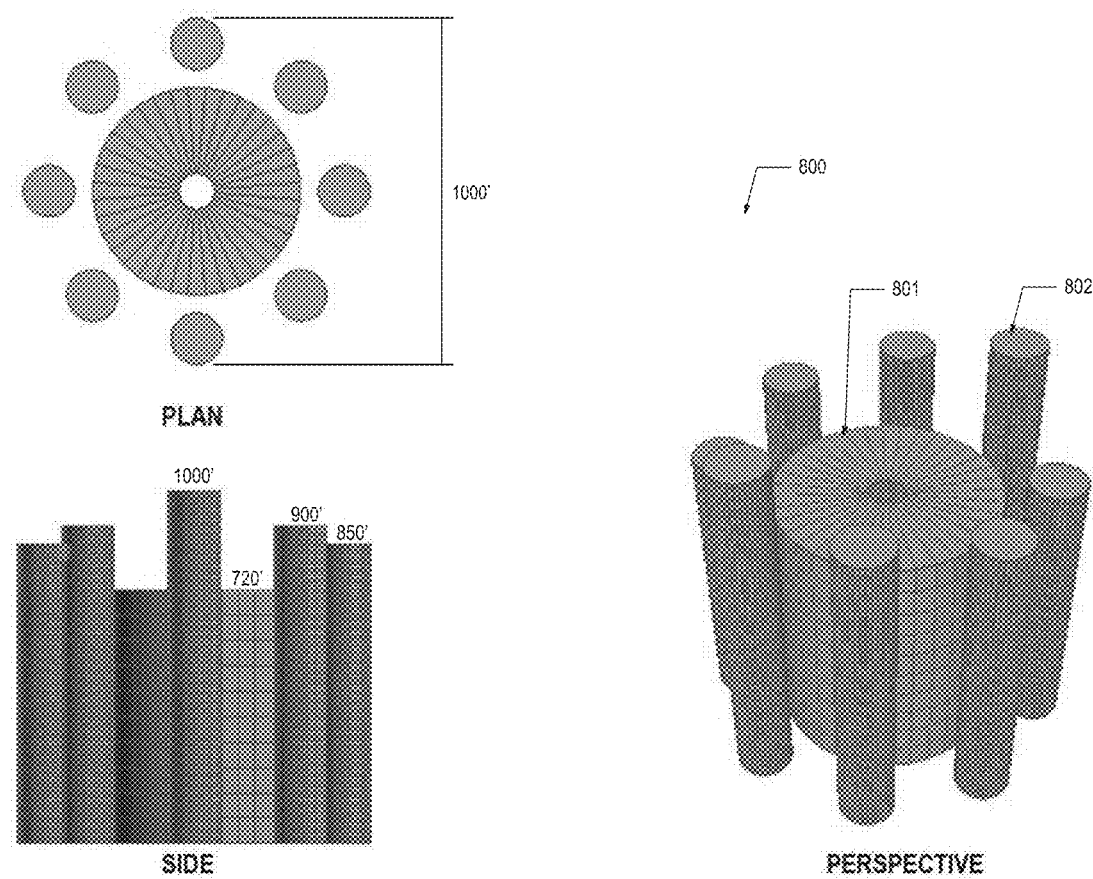
FIG. 8 shows a plan, side, and perspective view of a specialty building, in accordance with the present disclosure.

The illustration of FIG. 8 shows an example of a Specialty Building Complex 800. Each complex is comprised of a large volume high-rise central core 801 that may specialize in any one of the following themes, but not limited to this list: government, hospitals (healthcare), university (education), senior care (e.g. a center or facility), sports & recreation (e.g. with an arena), amusement & performing arts (e.g. a facility or center), shopping (e.g. a galleria with hotels); and museums. On the periphery would be located a number of residential towers 802, either attached or free-standing. The structure occurs below ground as well as above.

Figure 9:
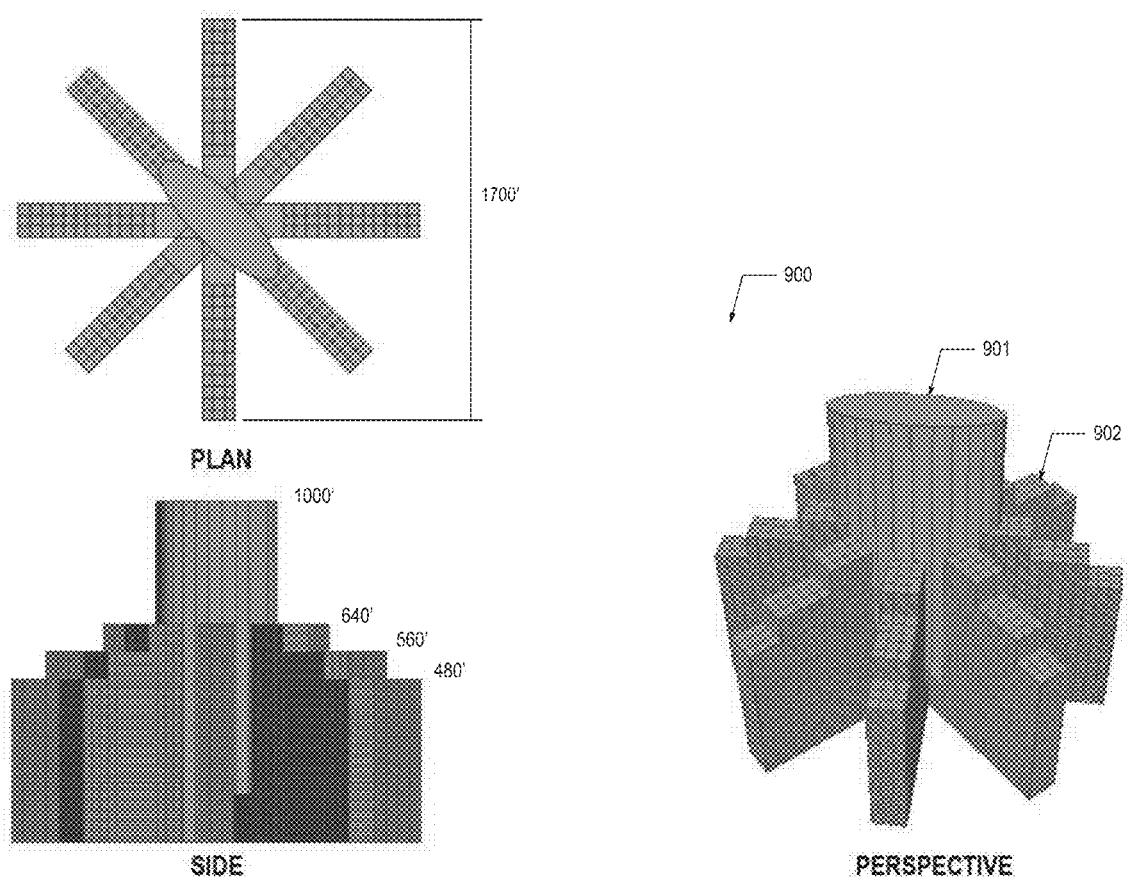
FIG. 9 shows a plan, side, and perspective view of a large modular Micro-City, in accordance with the present disclosure.

The illustration of FIG. 9 shows an example of a Large Modular Micro City 900. This complex is a mega-structure building with a large central high-rise tower 901, with smaller towers 902 surrounding this either attached or separate. This building complex includes a mixed-use feature that allows for work, residence, commercial and recreational activities. The structure occurs below ground as well as above. This complex is designed to have 35,000 to 50,000 residents.

Figure 10:
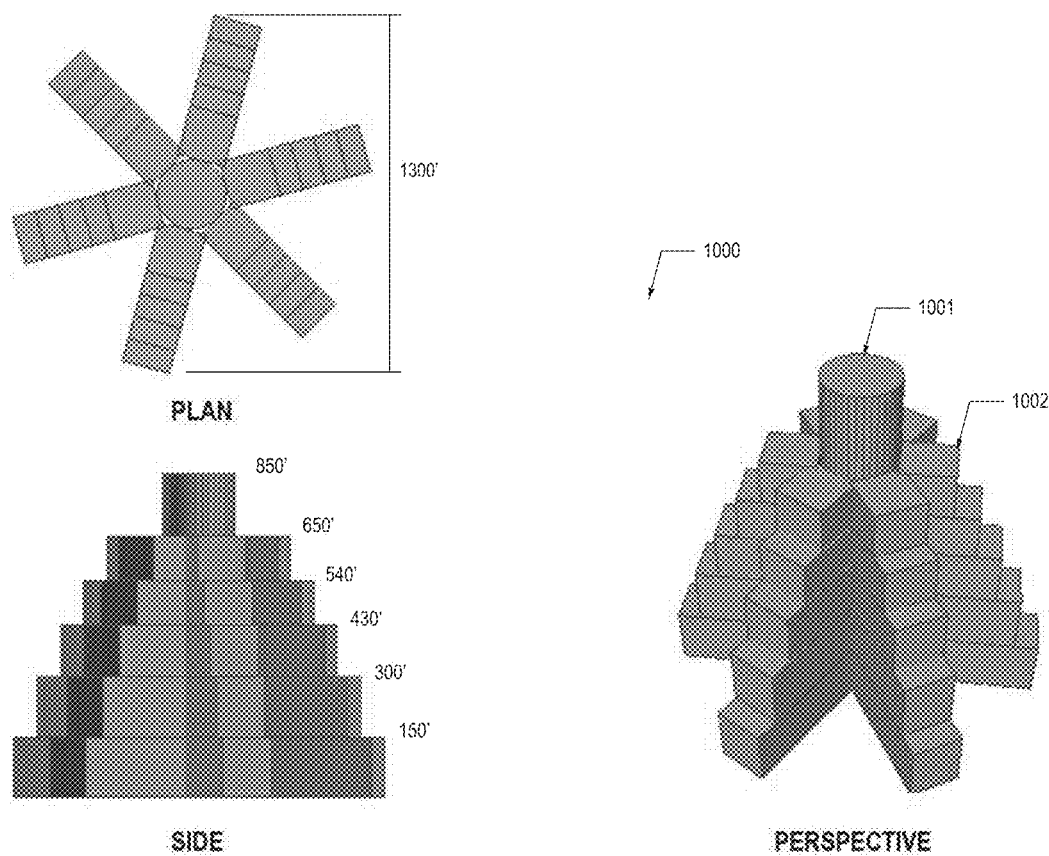
FIG. 10 shows a plan, side, and perspective view of a small modular Micro-City, in accordance with the present disclosure.

The illustration of FIG. 10 shows an example of a Small Modular Micro City 1000. This complex is a mega-structure building with a large central high-rise tower 1001, with smaller towers 1002 surrounding this either attached or separate. This building complex includes a mixed-use feature that allows for work, residence, commercial and recreational activities. The structure occurs below ground as well as above. This complex is designed to have 20,000 to 35,000 residents.

Figure 11:
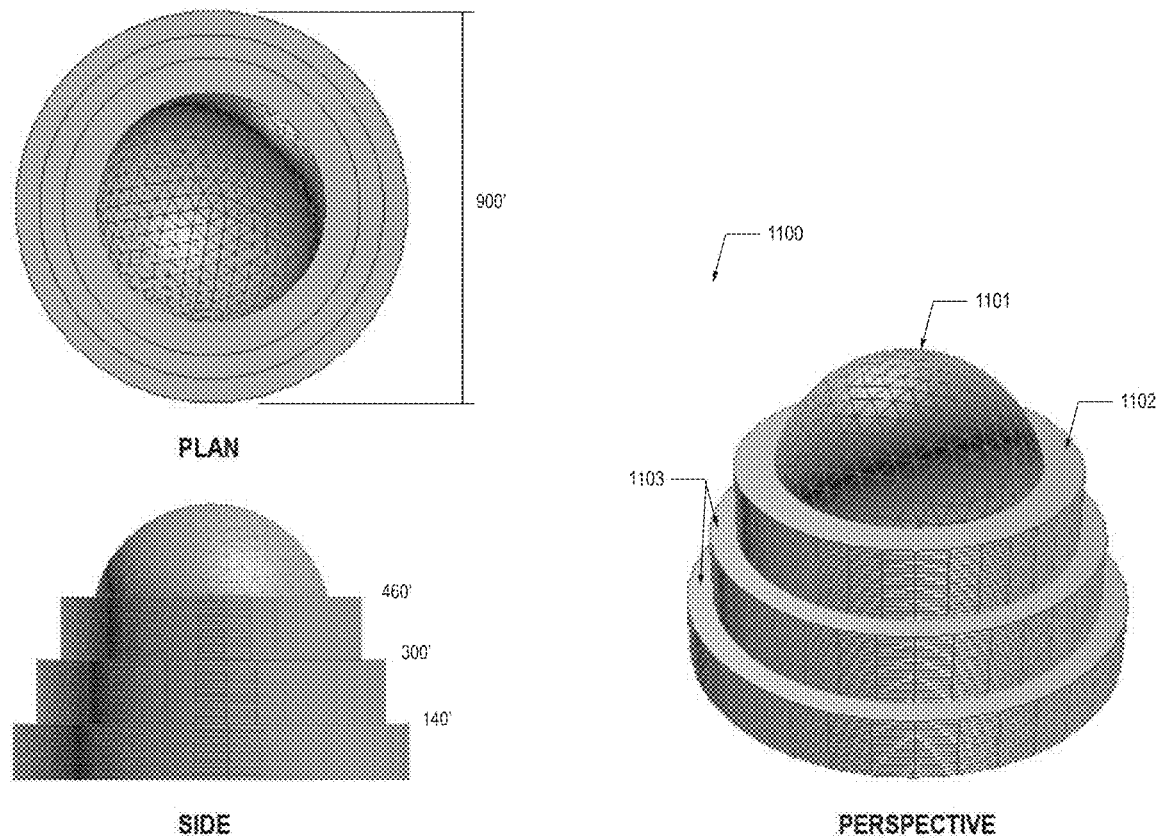
FIG. 11 shows a plan, side, and perspective view of an economy small micro city, in accordance with the present disclosure.

The illustration of FIG. 11 shows an example of an Economy Small Modular Micro City 1100. This complex is a mega-structure building with a stepped conical shape 1102 and 1103 (steps) with a geodesic dome in the center 1101 that may have separate structures surrounding this either attached or separate. This building complex includes a mixed-use feature that allows for work, residence, commercial and recreational activities. The structure occurs below ground as well as above. This complex is designed to have 15,000 to 25,000 residents.

Figure 12:
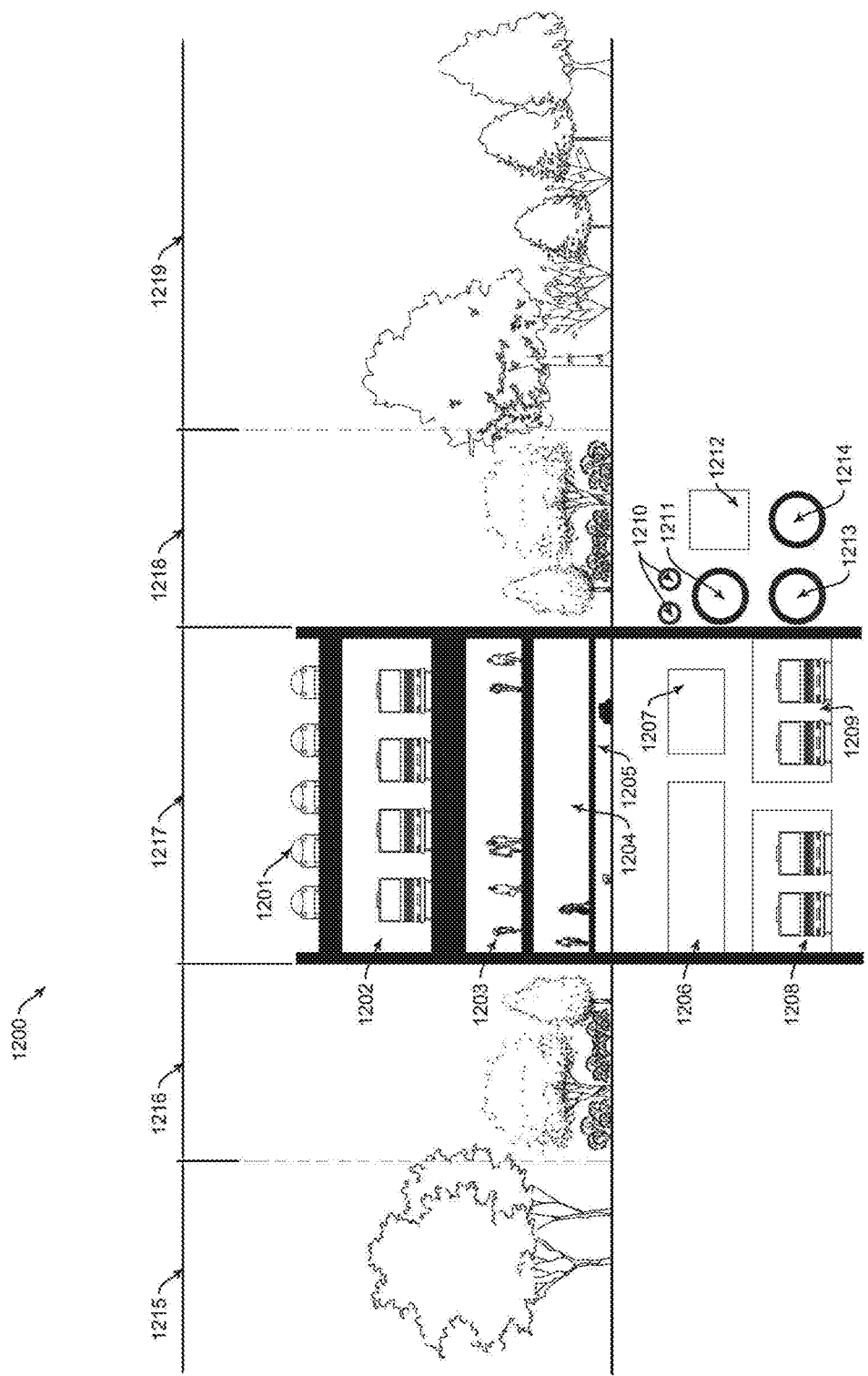
FIG. 12 shows a sectional view of a layered transportation corridor, the section taken along sectional line 12-12 of FIG. 2, in accordance with the present disclosure.

The illustration of FIG. 12 shows an example of a two-way, Layered Transportation Corridor 1200. It is comprised of multiple levels of bi-directional traffic. The uppermost layer is a roadway for zero-emission computer-controlled autonomous vehicles 1201 (driver-less taxis) that allow high-speed, non-stop transportation from origin to destination. Below is a mass transit to transit system 1202 that moves a large quantity of riders from every transit station in the Cluster City. Below this is an enclosed corridor that allows for both pedestrian and human-powered transportation 1203 to move short to medium distances within a controlled environment (HVAC & oxygen enhanced). The next level down 1204, is an open-air version of the enclosed corridor above. This allows for greater participation with the Wildness and adjacent landscaped areas. A very unique feature is the 4' high crawl space 1205 that allows wildlife to freely move through (laterally) and past this corridor. Hence, the corridor does not interrupt or impede free movement into Wildness zones 1219.

Underground is a pedestrian tunnel 1206 for two-way movement of people between Micro-Cities. There is another adjacent tunnel that moves food and other goods 1207 by conveyor along the tunnel. At the lowest level are two directions of heavy duty subway 1208 and 1209 that connects all the Micro-Cities to each other in "transit to transit" style. In addition, there is a large water transfer pipe 1210, piping for CO2 enriched air 1211 for the Vertical Farm, black-water sewage waste pipe 1213, a tunnel vault 1212 for electrical cables and fiber optic communication signals and a return air pipe 1214 for O2 enriched air from the herein disclosed Vertical Farm, all running along or beside a longitudinal (or circular) path of 1200.

The Two-way Layered Transportation Corridor 1217 has been designed to incorporate all roadways into one small surface footprint to reduce the space to a minimum as required for different pathways and hence return more land back to landscape 1216 and 1218 and wildness 1215 and 1219.

Figure 13:
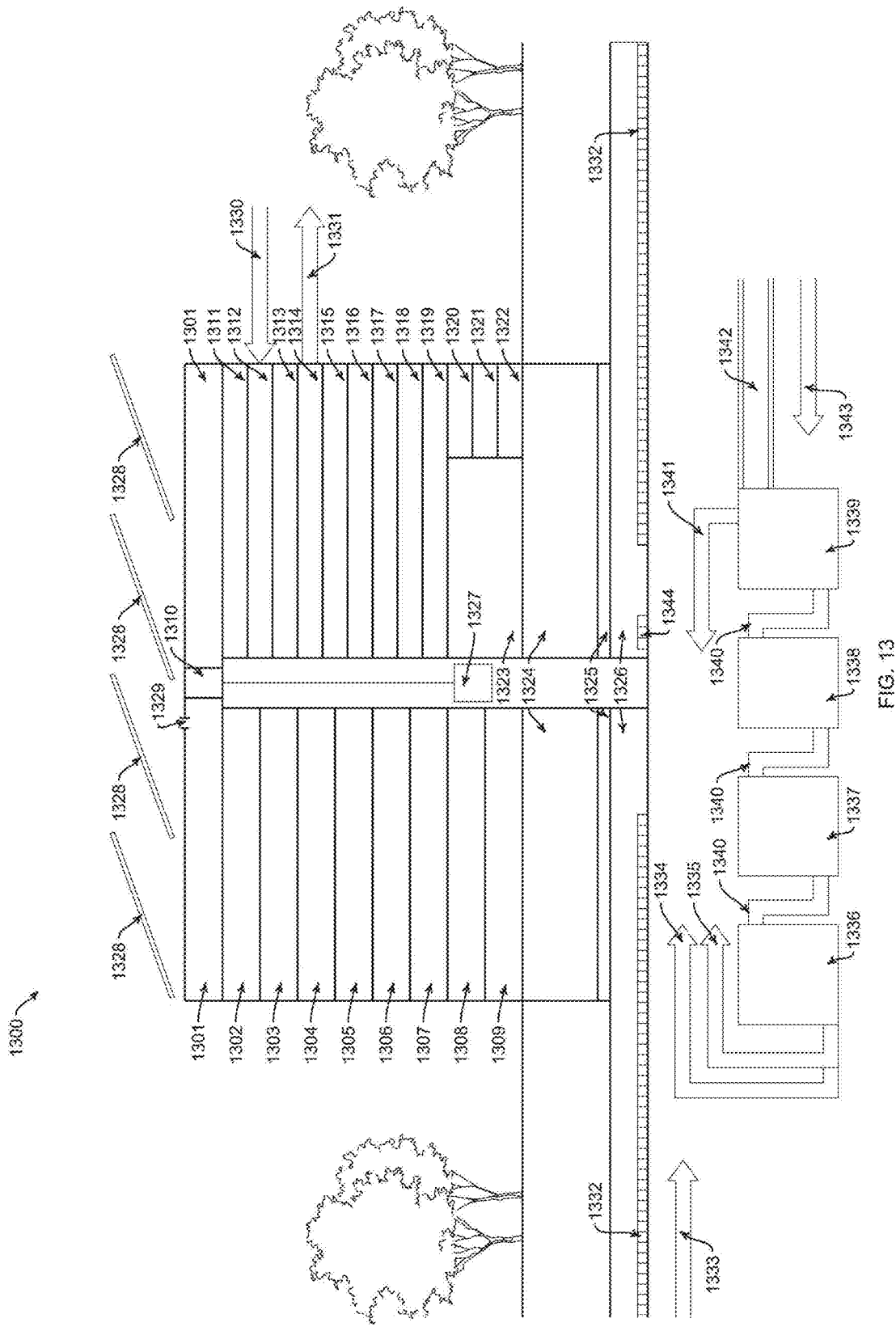
FIG. 13 shows a sectional view of a vertical farm and a waste recycling center, the section taken along sectional line 13-13 of FIG. 2, in accordance with the present disclosure.

The illustration of FIG. 13 shows a typical section of the Vertical Farm 1300. It is a very large structure that is circular shaped (circularly arranged), forming a very wide cylinder where most of all food consumed within the Cluster City is grown. It is to be understood that the various layers and floors shown in FIG. 13 run along the Vertical Farm structure (e.g. circularly or longitudinally, or intermittently or continuously). On the roof is a layer or floor including a large rainwater collection system with a drain 1329. Also above the roof are a series of solar panels 1328 disposed at the top of the Vertical Farm for receiving sunlight and generating solar-powered energy. Below the roof is layer or floor including a cistern 1301 that covers areas directly under the roof, except the elevator penthouse 1310. There are specialized plant growing areas on each floor or layer such as grape vineyards 1302, berry vines 1303, algae 1304, dwarf tree crops 1305, chickens 1306, milk cows 1307, steers 1308, aeroponics 1309, hydroponics 1311, vegetable crops 1312, soybeans 1313, corn 1314, wheat 1315, rice 1316, aquaponics 1317, sheep 1318 and pigs 1319. Separated from the food production floors is a packaging warehouse 1323 inside. The outside façade will have offices 1320, restaurants 1321 and fresh food markets 1322. In the middle of the building is freight elevators 1327 moving bulk food from each floor to food processing rooms 1324. Below processing is the packaging storage 1325 and shipping department 1326. Next to the shipping department are the underground conveyor systems 1332 that carry food to the Micro-Cities. There is also a circular conveyance system 1344 to moves food laterally from one area of the building complex to another. Included in the Vertical Farm System is CO2 enhanced air 1330 from the Micro-City buildings that is fed to the plants and oxygen enriched air 1331 that returns to the buildings.

Below the Vertical Farm footprint is the waste processing equipment that is totally separated from food production above. This Vertical Farm includes a triple power system with electricity from solar panels 1328 on the roof, clean methane power 1341 with CO2 & CH4 going into the plant atmosphere. There is also backup power from the Cluster City power system 1333. Organic waste 1342 from the Micro-Cities enters the anaerobic digester 1339, as well as solid waste organic matter 1343. For example, the anaerobic digester 1339 may anaerobically digest the waste 1342. After methane 1341 is extracted, the organic matter is pumped 1340 to the Aerobic Decomposition tank 1338. Organic waste from the Vertical Farm above is brought into this chamber as well, and then enzymes are employed to further break down the waste. Then it is pumped 1340 into another tank 1337 for drying and grinding. Once dried, the organic matter is conveyed into a sanitizing chamber 1336 where heat and ultra violet C radiation penetrate the matter while it is being churned. The dry matter is then conveyed either to the animal production areas upstairs 1335 as feed or dispersed outside on landscape and wildness areas as mulch 1334.

The illustration of FIG. 14 shows a cross section of a factory ring 1400, taken along sectional line 14-14 of FIG. 2 FIG. 14A shows the circular concept of a series of factory units 1410 existing in a vertical manner. The radial design pattern of 1410 allows for more equidistant commuting to reach the workplace (e.g. a distance between the factory ring and a ring of micro cities is convenient for commuters). It is to be understood that the various layers and floors shown in FIG. 14 run along the factory ring (circle) structure arrangement (e.g. circularly or longitudinally, or intermittently or continuously). For example, FIG. 14 shows the roof being both a water catchment basin 1408, with accompanying drain 1409. Under the roof is a large chamber which serves as a water cistern 1401. It may also have solar panels located on the roof to generate electricity. At the same level as the cistern are elevator equipment penthouses 1407 that provide mechanization to move materials and goods vertically on heavy duty commercial elevators 1405. The cistern may be sub-divided into special water treatment mixtures 1406 for use below. Rooms 1402 are regular factory areas, while 1403 are special use areas. The middle of the building, at ground level or below, will have a continuous freight loading area 1404, comprised of two sets of 2-way track for heavy usage, as well as periodic parallel loading spurs. In so doing freight handling will be uninterrupted no matter what the weather conditions are. FIG. 14 further shows entrance/exit rail tracks 1412 that connect factory indoor freight train tracks to main freight train lines outside the city. As such, the factory ring may transport freight or other goods and materials to other modules or cluster cities.

The illustration of FIG. 14A shows a 3-Dimensional perspective image of the Factory ring 1410 and the individual vertical factory units 1411.

The illustration of FIG. 15 shows the essence of Systems Design Programming for this improved city system. Under the unique Systems Design, the desired results are set as a goal and then it is back-stepped to the point of the existing or desired infra-structure. Development times must be extremely short as anthropogenic-forced climate change is occurring faster than most nations or civilization can adapt. We therefore have programmed this new city with an Integrated Tripartite design that includes the ultimate preferred elements of Ecology, Sustainability and High Performance to create an urban design more advanced than any and all previous work. For example, FIG. 15 shows a Venn diagram of three circles overlapping, the three circles each being "High Performance". "Ecological", or "Sustainable". In a high performance city, the city will have more economic efficiencies.

A high performance city will include digitally connected smart cities for greater human interaction, a protected transportation system to reduce commute time, communication and computer connectivity with fiber optics to all buildings, cyber security enhanced by organizing cloud storage in each Micro-City, a cluster city having a master smart controlled system including subset controllers tasked to carry out the majority of building control in each Micro-City, a city center that increases high-density interaction for over 200,000 people, a healthy and educated lifestyle and digital connectivity, and infrastructure spatial simplification providing greater efficiency than commonly existing cities.

A sustainable city is a city that protects its inhabitants from climate change effects, natural disasters and reduces impacts of pandemic disease. A sustainable city provides a constant supply of clean food, clean water, clean air, and clean abundant energy. A sustainable city is a resilient livable structure designed to withstand climate change and disasters, and works as a unified city to have organized disaster relief for inhabitants. A sustainable city also includes a security system preventing unwanted human intrusion and disease intrusion. Lastly, a sustainable city includes an air handling system using UVc sterilizing lights to disinfect air ducts.

An ecological city is a city having ecological harmony and mitigating neg-entropic aspects. For example, an ecological city is attributed with increased bio-diversity with over 50% dedicated space for "Wildness", and eliminates or reduces heat islands. An ecological city includes increased air flow. An ecological city has no cars (but in some embodiments zero emission autonomous vehicles are included), traditional trucks and most traditional roads, and instead uses electric mass transit to reduce greenhouse gas emissions. An ecological city produces electricity from renewable resources and nuclear power without producing any greenhouse gases. Waste heat co-generation in an ecological city provides more electricity and reduces or eliminates heat contamination. An ecological city may include a closed loop system that reduces an ecological footprint to under 0.4 gha. An ecological city eliminates waste outputs by using plasma incineration and/or bio-remediation, and may include a net zero water/waste system that eliminates the use of ground water.

Figure 16:
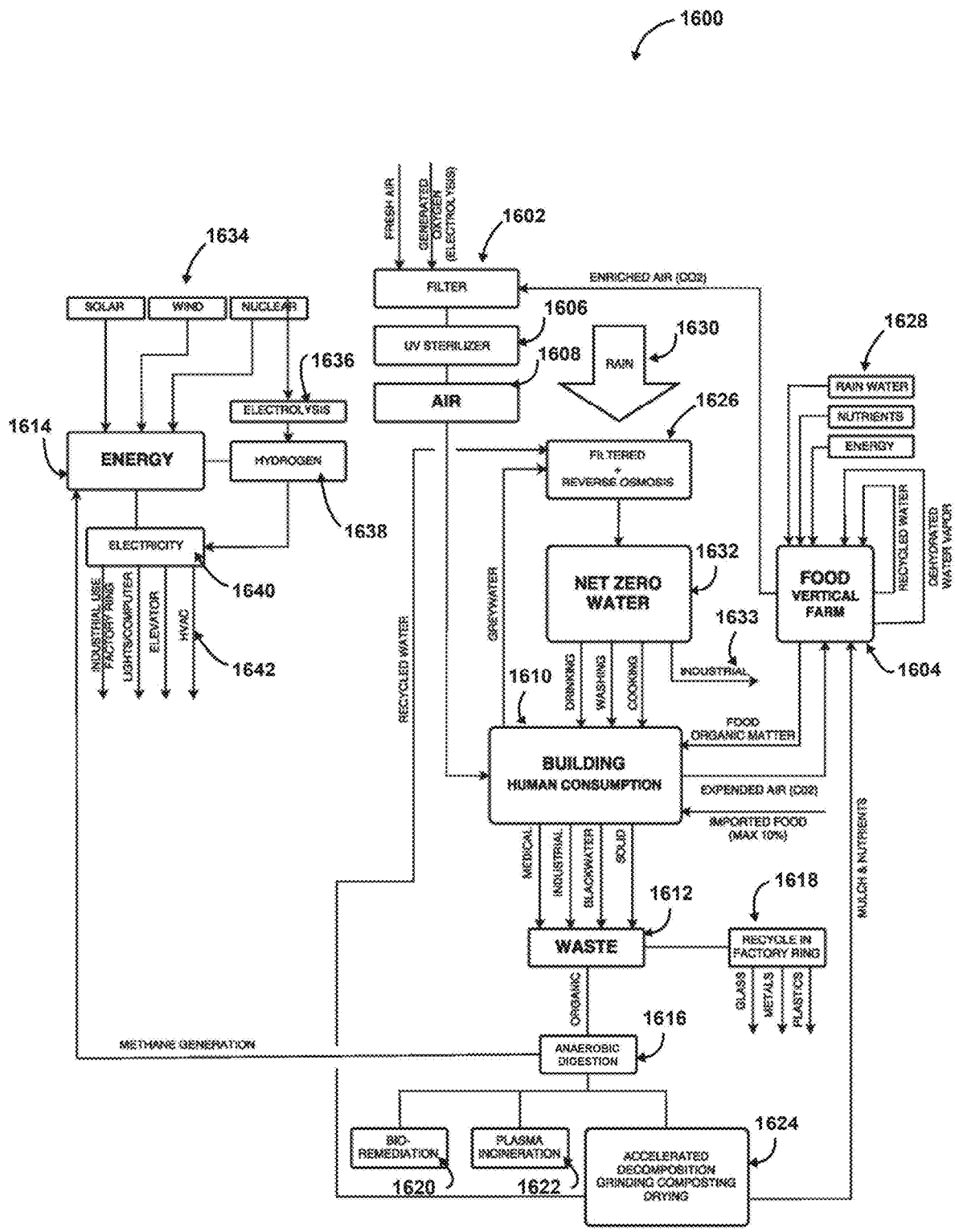
FIG. 16 shows a flow chart of a master process plan for a cluster city, in accordance with the present disclosure.

The illustration of FIG. 16 shows a Master Process Plan Chart 1600 that demonstrates the interconnectedness of the Main Necessities of Life: AIR, WATER, FOOD, ENERGY and WASTE RECYCLING with the BUILDING with Human Consumption being a key element.

This is an integrated design of the above elements to be self-sustaining and at the same time highly productive and ecological. For example, FIG. 16 starts out by receiving at a filter 1602 fresh air and generated oxygen (e.g. via electrolysis). The filter may receive enriched air (O2) from a vertical farm 1604 (from generating food). Received elements at the filter may then be passed through UV sterilization 1606 to become air 1608. The air 1608 is then passed to a building 1610 for human consumption. From the building 1610 expended air (CO2) is provided to the vertical farm 1604. Further, the building 1610 produces and provides waste 1612 (medical, industrial, blackwater, and solid waste). The waste 1612 is converted to energy 1614 via anaerobic digestion 1616 (organic waste) and methane generation. Some waste is recycled 1618 in a factory ring described above. The waste 1612 may be recycled to glass, metal, or plastic. Subsequent to the anaerobic digestion 1616 may be bio-remediation 1620, plasma incineration 1622, and accelerated decomposition 1624 (grinding, composting and drying). Subsequent to accelerated decomposition 1624, matter may be provided back to the vertical farm 1604 as mulch & nutrients and/or filtered as recycled water to a filtration and reverse osmosis process 1626. At the vertical farm 1604, water and dehydrated water vapor may be recycled within the vertical farm 1604. The vertical farm 1604 may receive rain water, nutrients, and energy at 1628. Rain 1630 may be received and filtered or processed via reverse osmosis at 1626. After being filtered, the rain 1630 is passed from the filtration and reverse osmosis processing 1626 to a net zero water element 1632. From the net zero water 1632, water is provided as drinking, washing and/or cooking water to the building 1610. Industrial water may also be provided from the net zero water 1632 for industrial purposes at 1633. It is also anticipated that greywater may be provided from the building 1610 to the filtration and reverse osmosis process 1626. The building 1610 may receive imported food (e.g. a maximum of 10% of total food), and organic food matter from the vertical farm 1604. Turning to the energy 1614, the energy 1614 may be produced via solar, wind, or nuclear power at 1634. For example, nuclear generated electricity may be processed via electrolysis 1636 to produce hydrogen 1638, which in turn stores energy to later produce electricity 1640. Electricity 1640 may be used for industrial purposes in the factory ring, for lights or computer power, for elevator power, and HVAC systems at 1642.

Figure 17:
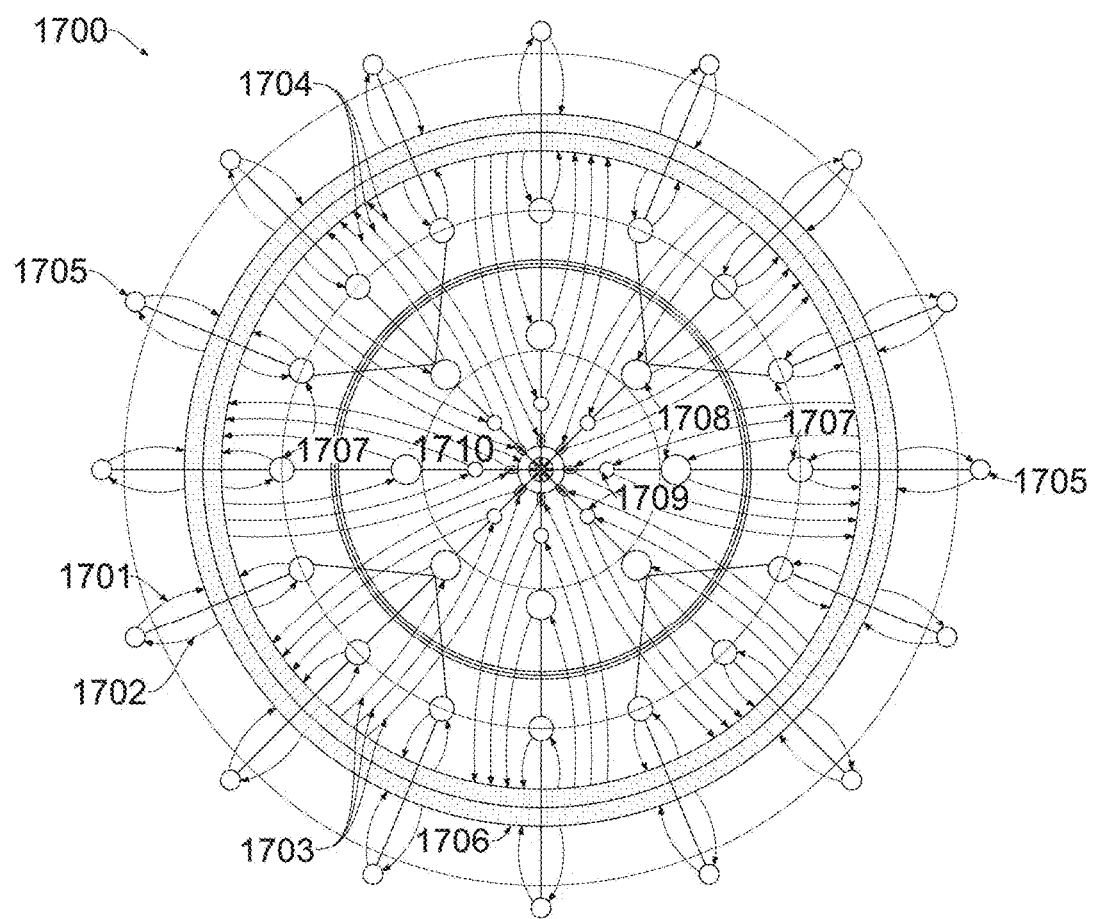
FIG. 17 shows a closed-loop recycling plan, in accordance with the present disclosure.

The illustration of FIG. 17 shows a plan 1700 that embodies the concept of Recycling of Materials from use to waste and reuse. Shown is a typical Cluster City with the flows of materials for each residential building. The Central City Core is at 1710. Specialty Buildings are at 1709. Large Micro-Cities are at 1708. Smaller Micro-Cities are at 1701. Economy Small Micro-Cities are at 1705. The Vertical Farm 1706 both generates waste above and recycles waste underground. A flow of Waste Material 1701 and 1704 goes from the Micro-City to the Vertical Farm. Food and oxygenated air flow from 1702 and 1703. At 1707 is a Micro-City. FIG. 17 may be directly related to the process plan shown in FIG. 16. For example, the arrows and processes described herein with respect to FIG. 17 may refer to respective elements of FIG. 16, such as directional flow of elements 1705, 1707, 1708, 1709 and 1710 to and from element 1706.

Figure 18:
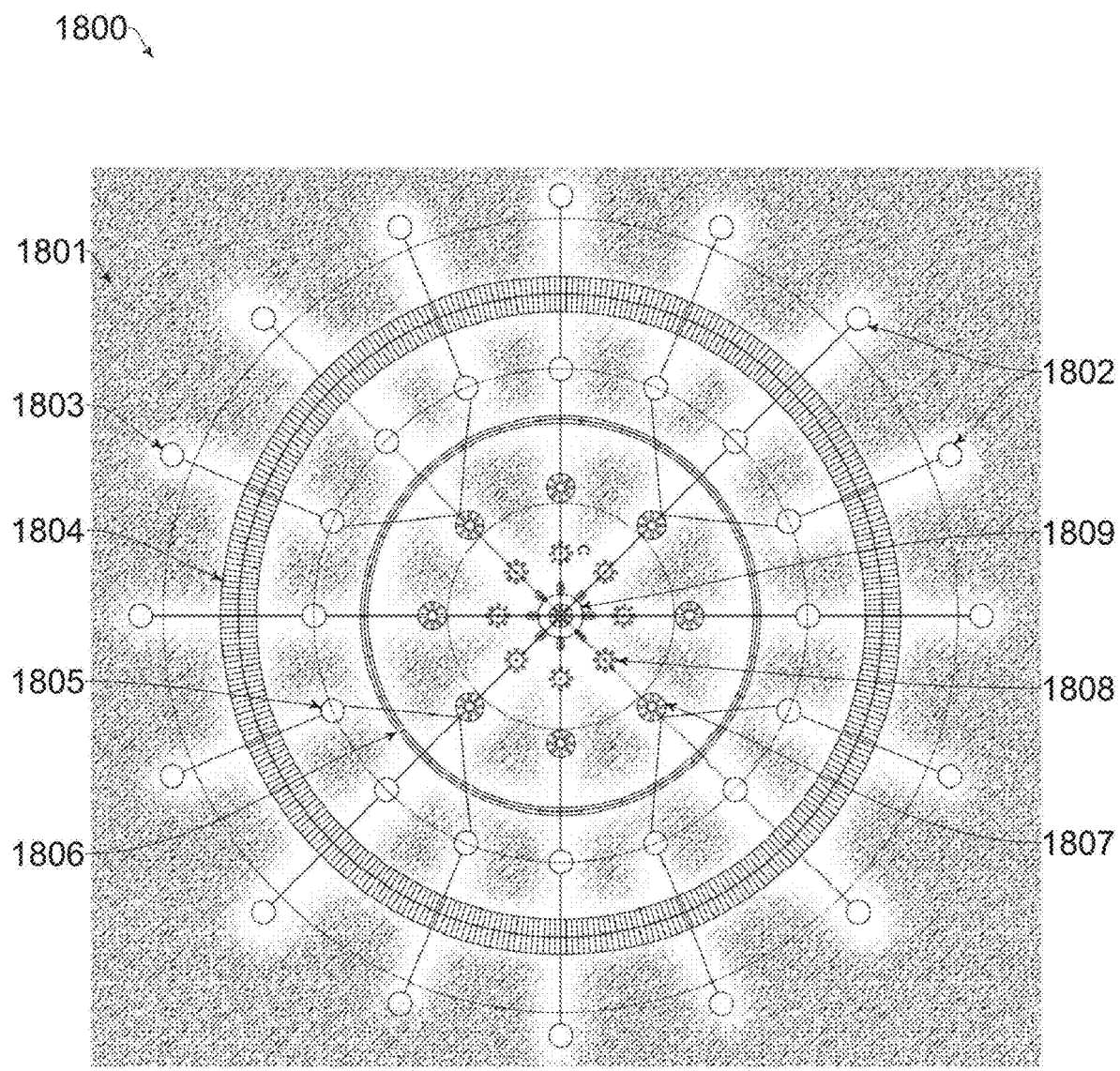
FIG. 18 shows a plan view of natural wildlife territory, in accordance with the present disclosure.

The illustration of FIG. 18 shows a plan of the Wildness Areas 1800 that shows "fingers" of Wildness which will extend from the perimeter of the City all the way to the Central City Core 1809. The hatched shading 1801 is land that will be protected from human intrusion. Two-way, Layered Transportation Corridors 1802 run circularly, as well radially. Common solutions for roads (e.g. prior art) roads would create a barrier preventing many wild creatures crossing to the other side, a disadvantage for ecological sustainability. However, in the present system, provided is a crawl space for smaller creatures to move at ground level under all the Layered Transportation Corridors 1802. These corridors allow for landscaped land next to them to be nature friendly. Beyond the landscape areas are thicket fences or water barriers that allow Wildness inhabitants to have little or no interaction with humans. Buildings, including the Vertical Farm 1804. Central City Core 1809, Specialty Buildings 1808 and Small Economy micro-City 1803 will be surrounded by these layers of landscaping and Wildness. Further, Micro-Cities 1805 and factory ring 1806 are shown in FIG. 18.

Figure 19:
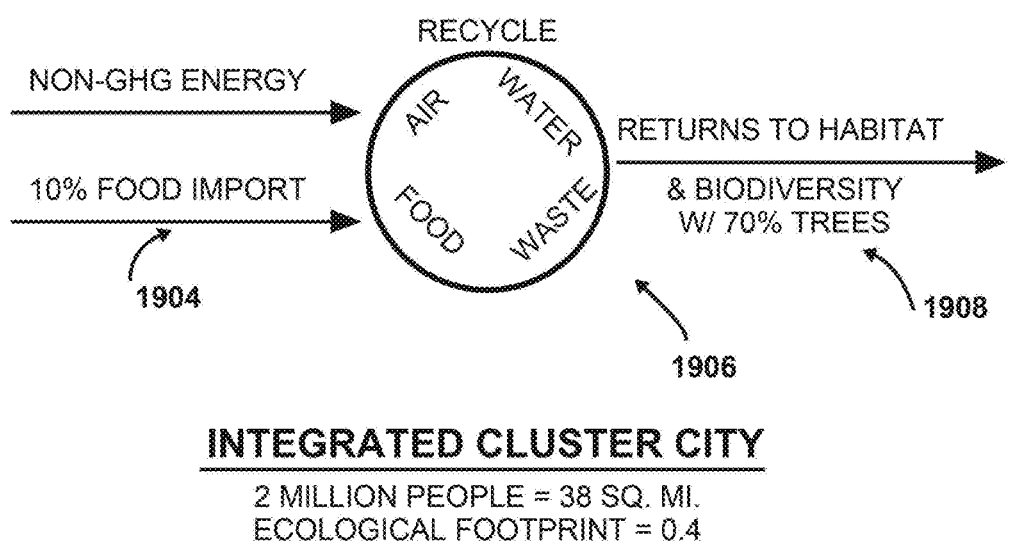
FIG. 19 shows a chart presenting the reduction of an ecological footprint, in accordance with the present disclosure.

The illustration of FIG. 19 shows a chart that schematically presents an Ecological Footprint of an Integrated Cluster City 1902 according to the present disclosure. The new Integrated Cluster City is a compact high-density city with approximately 10% of the land used for building structures. Air, food, water and waste are recycled resulting in little environmental impact. The energy input is local, and does not emit greenhouse gases. Most of the food is grown within the city limits, with only 10% imported for variety of consumption. Over 60% of the land within the city will be returned to Wildness to amplify Bio-Diversity. Over 70% of the exterior will have tree cover or water features. This city is depicted as having a physically small Ecological Footprint of about 0.4 gha. For example, at 1904, non-greenhouse gas (GHG) energy and imported food (e.g. maximum 10% of total food mass or calories) is inputted into the city system 1906. In the city system 1906, air, water, food, and waste is recycled. All waste is returned to the habitat (wildness) and biodiversity at 1908 in an ecologicaly sustainable matter as described herein.

It is to be understood that the above described circular arrangements (e.g. rows, rings, or circularly arranged sets) of structures or units may each include any number of structures or units. For example, a row or ring (i.e. a set) of circularly arranged Micro-Cities may include 2, 3, 4, 5, 6, 7, 8 or more Micro-Cities. Further, each of the circular arrangements may have any appropriate circumference, diameter or radius. For example, an inner circular arrangement adjacent a core may have a smaller radius than an outer circular arrangement. Further, the circular arrangements are not limited to being exactly circular, and it is to be understood that it is within scope and spirit of this disclosure that the circular arrangements may be ellipsoid, or generally non-circular or asymmetrical or conforming to hillside or water features. For example, in some embodiments the arrangements may be non-circular to conform and accommodate terrain variations and features (e.g. lakes, hills, rivers, coasts, or mountains). For example, in coastal embodiments where a central core building arrangement is disposed at the coast, the herein disclosed "rings" may resemble "arcs" since the rings would not be able to complete a full circle. It is to be further understood that the drawings may indicate exemplary distances between circular arrangements (e.g. they may be to-scale). Further, the various rings, rows, or circular or concentric arrangements of units or structures described above may be continuous or may be intermittent or have discontinuities in certain embodiments. It is to be understood that the various levels or floors shown in the sectional views may extend along, an entire circular distance of a circular arrangement, or may be intermittently disposed along the circular arrangements.

As such, the above system is based upon a new paradigm of organizing cities based on a Tripartite System where ecological concepts are integrated into real sustainability measures, as well as high performance economic efficiencies. This concept has a Set-Limit of city population growth with additional Set-Limit cities built nearby that are linked through transportation and communication links into larger defined regional centers.

High-density city design is achieved through vertical building technology of skyscrapers that are not only tall, but are organized into micro-cities of multiple towers integrated together to form extreme high-density mixed-use units inhabiting 25,000-60,000 people without the use of traditional (combustion engine) cars, traditional trucks and the chaos of typical street systems. These 20-100 story micro-cities are 1,200'-1,800' in diameter (mega-structures) and are separated by an average of about one kilometer distance. This allows growth to be vertical instead of horizontally sprawling unrestrictedly.

A Cluster City is comprised of numerous modular/programmable Micro-Cities that will achieve the desired population and type of productivity. In addition, they will have their buildings constructed with a Net-Zero Water System, full waste recycling within the boundaries of the Cluster City and have Vertical Farm food production that will meet up to 90% of the cities' food requirements.

The Cluster City is designed around a transit-to-transit transportation system that has a walkable distance to adjacent micro-cities. Use of light-rail, autonomous vehicles, walking and human-powered machines (bicycles) allow for movement above and below ground. As a self-contained-city, the Micro-Cities will have over 50% of occupants remaining within the city daily. Internal movement is vertically by high-speed elevator and horizontally by foot. The remainder of people will commute for work and visit nearby cities. They will be able to choose their transportation requirements with six ecological ways to get to their destination.

The primary foundation of these new cities is the orientation towards the Principles of Ecology to insure that all the inhabitants are living in balanced harmony with Nature, instead of contaminating Nature.

Under this new Cluster City design solid city sprawl is eliminated and replaced with intermittently located high-density Micro-Cities that occupy less than 10% of the Cluster City's area. The space between the Micro-Cities is then returned to Nature as dedicated "Wildness Preserves" land.

With most heat absorbing, hard-surfaces eliminated (roads, parking lots & buildings) solar energy is relegated to the production of photosynthesis within plant leaves. The absence of manmade hard surfaces eliminates the "Heat Island" effect where heat is absorbed in hard surfaces and remains all night instead of cooling over night with cooler mornings. This can result in a 3-4 degree C. difference in ambient heat.

Creation of an on-site food supply will greatly alter the impact of humans on the Earth by reducing millions of hectares under the plow, thus reducing an ecological footprint. This footprint measures the Earth's productivity per hectare versus consumptive use. Reduction of external farmland and Human Ecological Footprint of City will mean a tremendous reduction in the ecological stress that cities play upon the countryside. Cities will be able to reduce their impact on the Earth from an Ecological Footprint of 6.0-7.0 down to 0.4.

New Cluster Cities will be the most effective means employed anywhere on the Earth to mitigate human environmental damage and to restore harmony with Nature.

Sustainability is referred to as an integration of basic support systems that include the immediate environment of each building with the collective support processes of the immediate city so that the entire Cluster City becomes a self-sufficient, self-supporting entity not requiring external import of materials and the export of waste for the City to exist. These basic life support systems include:

AIR—the air we breathe must be balanced at 21% oxygen, 78% nitrogen. It must be held at 18-22 degrees C. temperature with 50% humidity. Filtering eliminates all pollutants (chemical, pollen, dust, mites, insects, bacteria & viruses). Oxygen enhancement will become necessary as the environment changes. These features are provided by the embodiments described above.

WATER—the improved city systems above will employ Net-Zero Water techniques to eliminate any use of ground-water sourcing to maintain the Micro-Cities; as well as all food production and manufacturing areas.

FOOD—the above described Vertical Farm technology will allow food to be created without the Sun. Clean energy LED lighting will be included to produce food through photosynthetic hydroponic and aeroponic techniques and perfect nutrient solutions that create food that is superior to organically grown techniques. Such eliminates the use of toxic chemicals to combat insect and disease pests.

WASTE—the Cluster Cities place waste within the realm of a circular economy. Solid waste is separated into metals, glass, plastics and organics. All waste is processed and placed back into the economy with much less new materials entering the city boundaries. Liquid waste is processed into water and solids, which are sterilized, separated, then dried and finally returned to the soil or into the food production system. Air Pollution is virtually eliminated with electric power generation from clean energy sources (e.g. nuclear) and monitoring of industrial processes.

ENERGY—energy requirements for the entire city (e.g. cluster city or micro-city) must also be considered. A factory city will require more energy for robotic assembly, handling of raw materials and finished goods. Food production consumes energy as artificial LED light is replacing sunlight. This requires considerable energy and a robotic system for plant movement. Air conditioning with its many aspects requires large amounts of energy. Lastly, an all-electric transportation system has a large energy footprint to power trains and autonomous vehicles. All demands of the City must be viewed for these 24×7 (constant) requirements.

These power demands need to be examined in terms of Base-load Power generation that is 24×7 (constant). This is the power that supplies 80%-85% of a city's energy requirements. Small Modular Nuclear (Uranium & Thorium) Generation IV units may be buried in the ground to provide power for the above described cities. Under this system there is no wasted fissile fuel (no radioactive waste storage requirements), no chance for meltdown and no energy loss from long-distance delivery. There will be abundant clean energy with none of the negative effects of 60 year old nuclear designs, none of the adverse atmospheric problems associated with burning coal, oil and natural gas.

A small modular nuclear reactor may be buried underground in a concrete and steel encased vault with ultra-high security. The reactor may be controlled automatically with no direct personnel in the facility in which the reactor is housed. A fissile charge may last for 10 to 20 years before requiring refueling. A Pebble Bed core design or other fissile delivery system may be applied to reduce or eliminate the likelihood of a nuclear meltdown. Helium gas heat exchange operations may be applied to eliminate the need of pressure domes that usually involve water. Helium is an inert gas that does not transfer radiation from a core to electrical turbines. Nuclear reactors may be placed in parallel to increase generated wattage according to energy demand. Fissile fuel may be produced from old stored Uranium or from thorium.

BUILDING—the design and technology to produce this lifestyle will require new designs of how a Mega-structure is engineered and how it functions for mixed-use. This will push technology into new realms of environmental containment, sensor detection, building envelope thermal and impact resistance, environmental controls, material flow, gas and heat exchange, elevator transport of large volume of people to higher levels and waste flow processing never before achieved.

Each Micro-City will require special architectural design to produce unique, living green (eco-friendly) entities that will enable humans to survive the coming environmental changes facing the human race in the near future.

HEALTH—it is the responsibility of the system design to optimize the health of the occupants. With health being defined as "the condition of being sound in body, mind, or spirit; freedom from physical disease or pain". The objective in this creation is for the system to create environmental stability that can buffer its citizens from the harm of a rapidly changing and degrading world. It is necessary that extreme conditions must be anticipated such that the built environment will be able to adjust to exterior environmental decay. New building standards need to be made that will predict increased Natural Threats to people and their built-environment.

SAFETY/SECURITY—the herein described buildings may be engineered and designed to withstand intermittent threats such as severe wind, hail, floods, fires, pandemic disease penetration and earthquakes. With proper design coastal facilities, including ports, the buildings and structures described herein will be able withstand Sea Level Rise for at least 100-150 years.

The buildings must be designed to protect against external threats both natural and man-made. Insects such mosquitoes, ticks, roaches and flies, as well as parasitic worms and rodents are vectors for disease transmission. Zoonosis can allow diseases to be transferred from pets and other animals in contact with humans. All portals must be employed to prevent entrance of disease carriers, while the buildings should be capable of being hermetically sealed on temporary and permanent basis as the need occurs. The air handling system shall be equipped with filters and UV sterilizers to prevent disease spread within.

In addition, the separation of Micro-Cities allows means to slow the spread of vector dispersed pandemic disease, chaos, mayhem and crime. It will minimize damage from terrorism and sabotage. This physical isolation will also assist in thwarting cyber-attacks and corporate subversion due to individual cloud formations.

Lastly, each Micro-City will maintain its own Resilience Plan for recovery from any damage and the overall Cluster City system will maintain repair equipment on-site to rework any damage.

Cluster Cities incorporate the following physical attributes. Cluster Cities are designed with modular Micro-Cities that are capable of being modified in size and location to achieve desired results indicated by the present disclosure. The high-density Micro-Cities flourish internally with high-speed elevators for vertical transport and pedestrian horizontal movement. The herein described Cluster City of 2.5 million people may occupy an area 125 km sq., yielding a density over 2,000 people/hectare while occupying only 10% of the land in an area the Cluster City generally extends through (e.g. a general area of the above described circular arrangement that forms the Cluster City) and providing additional use of 10% of the occupied land for food production (e.g. via the Vertical Farm). The Micro-Cities are located in concentric circular patterns, a walkable distance apart (e.g. radially) which optimizes rapid transit-to-transit mass transportation while allowing slower pedestrian traffic alternatives. Each Micro-City achieves a unique, showcased appearance that stands alone and is separate from other buildings within the Cluster City. As a mega-structure, the Micro-City includes a multitude of towers ranging from 20 stories to over 100 stories. The towers have internal and rooftop observation decks. The towers may connect to adjacent towers with Sky bridges also assisting in fire evacuation. The Cluster City has a finite completed size that is defined with boundaries to dismiss sprawl. Growth is continued through construction of adjacent Cluster Cities, each with a specialized, programmable functional design. Adjacent Cluster Cities are linked together with transportation and communications to form larger, Regional Cities. The Micro-Cities may be built at the least to 21st Century Green Building standards with abundant clean water and food, purified air and abundant non-polluting energy. The Micro-Cities are linked with Smart City digital communications and designed to easily accept new improved modification through trunk line fiber optics and city-wide Wi-Fi (wireless) transmissions. This will allow for immediate distribution of Knowledge and Culture through all digital portals. The Cluster City further links all the Micro-cities together with Smart City technology that will employ the most current building sensor control systems that cannot be retrofitted to older buildings. A major improvement is the layered transportation system which includes light rail, autonomous vehicles, human powered machines and pedestrian walkway; all on separated levels that reduces occupying the land surface. Extreme efficiency will dictate that not only the transportation time within the City be reduced but also inclement weather (rain; snow, hail, heat & cold) and air pollution (chemical, pollen and insect infection) be eliminated for each transportation journey.

The above system provides high-density mixed-use living environments providing peak work performance. The high-density living environments may occur in various zones of the Micro-Cities with periodic densities reaching over 2,000 people/hectare. This will make the Micro-Cities a network of the highest density work centers in the world, while injecting an Ecological Environment in between to reduce stress and tension.

This urban network of Micro-Cities is from a broad perspective similar to an electronic LAN communication system with smart computer terminals linked into a master system (Cluster City) whose total computing power and efficiency can become exponentially stronger.

A major efficiency component of these new cities is the radial approach of the Micro-Cities within the context of a circular Transit-to-Transit transportation network. By reducing the area of each Micro-City, the distance to a Metro Station is kept to a minimum maximum of 500 m) while allowing a maximum number of riders' access to both directions in above and below ground transit. By providing all occupants short distances to Metro Stations greater ridership and dependence on the system for transportation will lend city occupants to use the system more frequently. With many people commuting to different work locations from where they live, transit time efficiency allows for either more work or more personal time.

One of the elements of the Transportation System is the Autonomous Vehicles. These vehicles may require sensor embedments in road surfaces to operate autonomously. The transportation system for 2.5 million people will be accomplished with about 220 km of layered transportation corridors.

Cost cutting techniques may be employed in the Micro-City design that allows low cost smaller towers to spread the footprint of the mega-structure so that the taller towers will be anchored to a larger base and reduce the cost of the moment connection anchoring. Likewise creation of monolithic foundations can be utilized to stabilize each of the component towers and hence reduce costs.

By using modular designs of mega-structure components both the initial construe costs and the maintenance costs can be reduced.

It is anticipated that higher construction costs of the high-rise elements can be offset by the addition of low cost mid-rise towers and by the reduction of many eliminated elements (roads, bridges, street lights, stop lights, pipes, and wire) of the infrastructure.

By having much greater system efficiency and higher productivity there should be an improvement of 20%-30% over current, existing cities. The efficiency profits can be used to offset increased investment expenses.

High-density cities, like the Cluster City, may be feasible with an ideal balanced distance between Micro-Cities that allows for both pedestrian ground movement and transit to transit stops. Further, the herein described protected transportation structures and enclosed cities will protect inhabitants from climate change and traditional weather.

The system may include Greenhouse Gas-free energy systems, such as the new Generation IV nuclear reactor designs or the like created in factory reproducible Small Modular Reactor units that are buried within the ground. Renewable energy sources (solar & wind) may be used to supplement the system during peak hour requirements.

It is anticipated that coastal Cluster Cities will include perimeter walls to protect against sea-level rise. Further, the towers or structures above may be shaped aerodynamically to increase air flow within the cities and subsequently to eliminate heat islands. The aerodynamically shaped towers, radiating canals, and wildness areas may be shaped specifically to direct wind and reflect the absorption of solar energy into the Earth.

In some embodiments, a water cistern may be located at a bottom of any of the herein building facilities to store purified water. Any of the herein disclosed buildings may be insulated, and the cistern may act as a geo-thermal heat stabilizer for stabilizing temperature variation inside the buildings. Air humidity variation inside the building structures may be eliminated or reduced with by including or employing dehumidifiers that return moisture from human respiration into the water supply. Human exhausted air may be scrubbed of CO2, which may be piped into the Vertical Farms, and thereafter supplemented with new O2 from an electrolysis generator.

The Layered Transportation Corridors may connect all modular structures within each cluster above and/or below ground level. Disposed above the ground may be pedestrian and pedestrian wheel-powered enclosed pedestrian walkways, elevated light train or monorail, automation vehicles and cable gondolas. Disposed below ground may be pedestrian subway, freight subway, food & waste conveyors, power & communication cables, water pipes, air ducts, and pedestrian walkway tunnels. The factory ring may include adjacent stalls (internal building separations) or include consecutive buildings that comprise the factory rings. The overall size of the factory ring complex may be related to government requirements for factory production. Such factory buildings may be designed for expansion by increasing their height. The factory ring may contain a heavy freight train transportation system in the middle of the structure to move raw materials in and finished goods out. Freight elevators may be placed in each factory sub-unit to transport materials to the train system located below. Industrial heat and waste evacuation (solid & gaseous) may be available to each individual factory sub-unit.

The city systems may allow movement vertically via high-speed elevator locomotion within each micro-city or single-use tower. Movement of goods and materials may be accomplished on different sub-levels so as to not interfere with human movement. Movement of goods within the city may be accomplished via power-assisted vehicles. The factory ring may provide a proximate location for manufacturing, industry, and jobs relative to housing in Micro-Cities. For example, workers may be provided housing in Micro-Cities that are within walking distance of provided jobs for the workers, reducing long, and energy consumptive commuting.

The vertical farm ring may provide a reliable supply of food for all inhabitants. The food may be free of contaminants and nutritionally rich in the basic building blocks for supporting human life. Through algae production plant nutrients required for hydroponic and aeroponic growth may be created by the vertical farm structure(s). Dehydrated sludge and solid waste may be mechanically transported to the vertical farm structure where aerobic and anaerobic decomposition occurs. The farm roof may include a collector of rainwater that is dispersed back to all of the Micro-Cities. Waste containing heavy metals may be placed in bio-remediation tanks where plants and algae utilize the waste for food and end up purifying the remains, which may be dried and applied to soil to increase organic composition.

The above described ecological, sustainable, and high performance cities may replace existing cities in all locations. For example, the cities may be created from farmland near existing cities or through demolition of segments of existing cities until complete replacement is established.

The cluster cities may have a medium density of 5,000 people per square kilometer or a high density of more than 25,000 people per square kilometer. The density of the cities may be rated as property limits of the Cluster City (e.g. set by government or computer regulation). The population of a Cluster City may be between 0.4 to over 3.0 million people with Micro-City populations of 10,000 to 100,000 people.

The cities (e.g. Micro or Cluster cities) may vary from financial centers, manufacturing centers, mining centers, agricultural centers, resort/tourist centers, fishing centers, forestry centers, mountain centers, recreational/amusement centers, educational centers, high-security centers, medical/health centers, and shipping centers. The geographic location of the cities may be adjacent rivers or lakes or in plans, valleys, mountains, deserts, or islands. The cities may act as harbors and may be located in coastal regions or near seashore. The cities facilitate cultural or ethnic uniqueness while allowing inhabitants to flourish and survive climate change perturbations. The cities may provide opportunities for a wide range of wealth classes (e.g. upper, middle, lower). Most inhabitants may be required to obtain a minimum of 10 years of basic education, and may be provided college, university, and doctorate degree opportunities.

The modular Micro-Cities and single-use towers may integrate into a larger Cluster-City with their own central government and economy. The Cluster cities may be designed in many different variable forms depending on national and regional central planning requirements.

The Layered Transportation System for each Cluster City may be built as a functioning concentric ring (either circular, ovular, or elongated) with functioning portal stations operating to completed micro-cities for transporting inhabitants. The herein described transportation systems will occupy a minimum space at ground level and instead use multiple stacked levels, each level being dedicated or devoted to a mode of transportation. This stacked arrangement maximizes transportation capacity while minimizing ground surface area required for the transportation corridor. For example the transportation system provides various modes of transportation within a tightly defined corridor of stacked levels. This configuration narrows or focuses human presence for transportation such that more land is returned to nature. The transportation corridors will exist both above and below ground on a same or different footprint. The Cluster Cities limit a horizontal sprawl by including 20 to 150 floor buildings above ground in very high density. The Micro-Cities position high-density footprints with great open space between them, returning space and land back to nature (a feature known as Retractable Development). This feature allows "wildness areas" to repopulate with many species normally, denied their original habitat by prior city systems. Such wildness areas also act as segregation barriers that may stop or slow pandemic disease from spreading. The structures may have security entrances (portals) that thermally scan and test inhabitants for disease. Additionally, the security portals maintain separate or block air flow from entering into the rest of a Micro-City, since the Micro-Cities are sealed from outside air contaminants.

The vertical farms may be fully automated with robotic controls of temperature, moisture, water, nutrients, pH levels, light, and gases. All growth activities may be monitored and controlled by a computer program to enhance the nutrition of the food grown. Vertical farms exist in a circular format to minimize a distance from Micro-Cities that food and waste must flow.

A single location may be determined in each Cluster city to build and maintain an underground, small modular nuclear facility which may have an underground micro-grid power supply directed to all Micro-Cities (mixed-use), Single-Use structures, Factory Ring, and Vertical Farm structures within each Cluster city. Using such nuclear energy provides an uninterrupted supply of renewable energy for inhabitants within each Cluster City, virtually no energy loss in transmission from the source of the energy to users, industrial heat for production of steel, aluminum, glass and cement, a heat source for electrolysis that separates water into breathable oxygen and hydrogen for mobile fuel cell operation, cogeneration of waste heat using a Rankin turbine electrical generation process, and reactor heat evaporative distillation of seawater for pure water for injection into city water supply.

It is anticipated that a computing system may be included to control building or constructing the various structures described herein. Such a computing system may control and regulate the acquiring, processing, distributing, and consuming of resources. Further, the computing system may regulate the various transportation systems described above to safely transport goods, commodities, products, building materials, and/or inhabitants. As such, the computing system may include various sensors to determine the appropriate distribution, control, or regulation of any of the above elements, commonly known as smart cities.

In conclusion, an ecological, sustainable, and high performance city system is disclosed, the system being configured to improve economic efficiency and performance. The system may comprise a plurality of concentric micro-city rings arranged for concentrated human living and surrounding a central core building arrangement, each ring including a plurality of micro-cities. The concentric micro-city rings may be configured to: allow transportation of goods and people at high speeds without cross-traffic interruptions of single level intersections, allow increased traffic flow while maintaining a same relative velocity by reducing intermodal space of low speed traffic, the low speed traffic being pedestrian traffic or human powered vehicle traffic, allow transporting small containers of goods intra and inter-city autonomously in a particular autonomous transportation level, allow human powered movement within each micro-city and between micro-cities due to short distances and time durations between journeys, allow a higher volume and activity of vertical people movement relative to horizontal people movement, allow over half of all driving activities to be short distance for school, groceries and/or entertainment without leaving a micro-city, while longer inter-city trips to work are executed via rapid transit and autonomous vehicles in short durations, and allow a higher density of human occupancy that creates more human interaction allowing for more business and social contact frequency.

The system may include a building arrangement, the building arrangement having building elements, where the building elements have a modular configuration allowing for system interchangeability, and the building elements may have: a varying height, shape, volume, and human density, varying locations of office and residential buildings, and varying locations of food and factory rings.

The micro-cities may provide improved security via a nodal configuration, the nodal configuration providing space between adjacent micro-cities, where the improved security may be facilitated by: physical security structures configured to isolate crime within a small and localized population to reduce crime incidence, and cyber-security systems localized and protected via isolated control of operation that is configured to be off a grid.

The central core building arrangement may be predominated with very high density office and residential populations to stimulate greater human activity and connectedness. The city system may be configured to provide a building environment configured to protect inhabitants from pollution. The city system may include air purification and recycling systems within each micro-city to keep occupants healthy by keeping the occupants from breathing harmful impurities and harmful biological agents of outside air. The air purification and recycling system may be supplemented with extra oxygen, wherein each micro-city provides occupants with purified and recycled water for reducing ingested harmful contaminants found in groundwater sources, the water being provided via a constant water supply regardless of how scarce external water resources are.

The system may include at least one radial transportation corridor radially configured for providing transportation between the micro-city rings and the central core building arrangement, the transportation corridor having environmental enhancements to allow comfortable movement on pedestrian and human powered levels to counter undesirable outside conditions, and at least one non-radial transportation corridor ring configured for providing transportation between micro-cities in each micro-city ring. A micro-city may include a system for providing clean and non-polluting locally produced energy via the implementation of: micro-grids to eliminate power loss in long-distance transmission, base-load power supplied by small modular nuclear reactors, high-temperature generating systems for industrial production of steel, aluminum, glass, and cement, and using renewable resources such as wind and solar for peak energy demands.

The city system may be configured for providing ecological harmony such that: ecological balance is achieved within city limits, land is returned back to nature such that unused land is returned to native growth and wild animal populations, such that high density micro-cities use approximately 10% of land compared to current low-rise sprawls, such that a layered transportation corridor uses 1% of land compared to current surface road systems having equivalent traffic volume that use over 30% land space, heat islands are reduced by eliminating road and parking lot surfaces to return land for growing foliage which converts heat into plant material, and by reducing building surfaces exposed to sunlight by incorporating trees onto buildings, using roof gardens, and by increasing building height to surface area ratios, thus reducing constant roof surface exposure, such that air flow is increased via implementing less overall surface area to smaller tall buildings, such that there is much more open space between large tall buildings allowing more horizontal air flow movement to reduce trapped heat, such that building presence is only approximately 10% of total area of a cluster city, turning hard building surfaces into softer areas to return land back to forests air flow is increased via implementing less tall buildings such that buildings contribute less to horizontal air flow movement and reduce trapped heat, and such that building presence is approximately 10% of a total area of a micro-city.

Lakes, ponds, and streams may be created to act as heat buffers allowing more surface air flow. Solid and liquid waste recycling may be achieved by chemically reversing existing landfill processes through heat and bio-chemical interaction. Packaging of food may be changed to support ecological harmony by altering food production systems, land used for supply requirements may be reduced reduced, farmland may be returned to nature, where plant production with harmful chemicals and saline water introductions may be stopped and feedlot contamination for animal production may be stopped, forest reduction may be slowed via greater replanting and reducing or eliminating the use of trees for products or as building materials, surface and ground water may be allowed to return to a natural balance, less mining may be done and tailing, may be returned into tunnels, atmosphere may be renewed by reducing carbon dioxide and greenhouse gas production. Land, rivers, and lakes may receive much less discarded pollutants such that water systems may be prevented from being contaminated and an ecological footprint of a city may be 0.5 or 0.4 hectares per person compared to traditional cities having 6.0 hectares per person for a same population number.

The system may further comprise at least one factory ring and at least one farm ring, where the factory ring allows for commercial production and distribution of goods within a concentric micro-city via: non-interrupted two-way concentric rail tracks, one or more continuous entrances and exits for self-motive train cars that merge goods into a parade for loading and unloading goods along main tracks, and one or more manufacturing plants that are configured to receive raw materials and produce value-added labor and expel goods in a routing system for further completion or end-use distribution.

The system may further comprise at least one factory ring and at least one farm ring, wherein the farm ring produces locally grown indoor hydroponic and aeroponic food that is free of harmful chemicals that are typically used to defeat insects and disease, the food being free of the harmful chemicals to maximize worker output, wherein the farm ring provides a constant supply of fresh food grown 365 days a year without being affected by aberrant climate variables, insects, disease or pollution, and wherein the farm ring implements energy efficient food production techniques and food varieties for obtaining proteins, carbohydrates, fats, and vitamins as needed for human health and well being.

As such, in some embodiments the methods or tasks described above may be executed or carried out by a computing system including a tangible computer-readable storage medium, also described herein as a storage machine, that holds machine-readable instructions executable by a logic machine (i.e. a processor or programmable control device) to provide, implement, perform, and/or enact the above described methods, processes and/or tasks. When such methods and processes are implemented, the state of the storage machine may be changed to hold different data. For example, the storage machine may include memory devices such as various hard disk drives, CD, or DVD devices. For example, data may be stored for developing big data analytics for greater digital control. Also various cloud storage systems with cyber attack defenses may be included in the Cluster Cities or each Micro-City, or any structure or element thereof. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI) or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, keyboard or gaming controller. For example, a user input may indicate a request that certain task is to be executed by the computing system, such as requesting the computing system to display any of the above described information, or requesting that the user input updates or modifies existing stored information for processing. A communication subsystem may allow the methods or tasks described above to be executed or provided over a computer network. For example, the communication subsystem may be configured to enable the computing system to communicate with a plurality of personal computing devices. The communication subsystem may include wired and/or wireless communication devices to facilitate networked communication. The described methods or processes may be executed, provided, or implemented for a user or one or more computing devices via a computer-program product such as via an application programming interface (API). In some embodiments 3D holographic, augmented reality, or mixed reality computer systems may be included. For example, augmented reality computing systems may display 3D holograms or computer renderings in real space, such as in designated holographic rooms or in the various office or specialy facilities described above. For example, augmented reality holographic systems may be included for communication, productivity, or recreation.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An ecological, sustainable and high performance city system, where the system is configured to improve economic efficiency and performance comprising:

(a) a cluster city as the primary organizational pattern of functional groupings of buildings
(b) a plurality of concentrically arranged micro-city buildings for concentrated human living with over 5,000 people per square kilometer and surrounding the central city core,
(c) a compact spacing to allow for increased walk-ability of distances from 2,000 feet to 5,000 feet for both concentric curvilinear transportation corridors and radial transportation corridors, the concentric, circular pattern creates greater equidistant destinations for walk-ability, while maintaining sufficient distance for proper mass transit stops,
(d) a Micro-City building larger than 1,000,000 sq. feet area that comprises residential living, as well as typical mixed-use daily travel activities internalized that had been previously completed by the car, a such as: going to work, getting food, going to school, going to church, going to see friends, going to health treatments, going shopping for clothes and furnishings, going for entertainment and going to meetings, incorporating these activities into a micro city building allows implementation by means of indoor pedestrian horizontal movement and elevator vertical movement, thus eliminating the use of cars and trucks, as well as most outdoor travel,
(e) allows a higher volume and activity of vertical people movement relative to horizontal people movement
(f) allows human powered movement within each micro-city and between micro-cities due to short distances and time durations between journeys;
(g) a plurality of specialty buildings that are themed-oriented providing a specialty experience,
(h) a plurality of conveyance means where the layered transportation corridors are configured for two-way transportation, The structure has multiple layers to provide a safe separation for various forms of human movement based on speed and vehicle weight comprising:
walkways—100 kg×10 km/hr
human powered—120 kg×20 km/hr
elevated mass transit—150,000 kg×100 km/hr
autonomous vehicle taxi's—2,200 kg×120 km/hr
pedestrian tunnels—100 kg×10 km/hr
subway mass transit—200,000 kg×100 km/hr
(i) a layered transportation corridor with the pedestrian and human powered vehicle levels protecting humans from impact with other vehicles;
(j) inclusion of two-way mass transit, both concentrically and radially allows for large high-density movement of people from one Micro-City transit station to the next within the framework of a compact, concentric city,
(k) a series of transit station to station orientated buildings insuring a simplified system with people traveling to their destinations faster with less walking; and without weather inconveniences by never leaving a protected environment,
(l) a Cluster City with a plurality of transit oriented concentric circular patterns with radial connectors eliminating the need for other surface roads, the full amount of layered transportation corridors totals less than 300 km of linear surface within a complete cluster city,
(m) a factory ring comprised of:
a modular ring-shaped building with a minimum radius of 1000' within the cluster city,
the factory ring receives raw or incompletely assembled materials and produces value-added labor, expelling goods for further completion or end-use distribution;
a factory ring receives used goods to be recycled by disassembly into component parts which may be re-assembled into different assemblies or the re-useable parts are expelled through distribution to another location,
a ring-shaped factory operates an indoor environment to sustain work during inclement outdoor conditions and polluted air,
a plurality of segmented work domains separating different types of operation,
a plurality of concentric railroad tracks in the middle of the ring-shaped building allowing two-way movement of freight cars,
a track switching control to position individual freight cars into loading spaces,
each work domain has a train unloading space to remove standard shipping containers and reorganize into smaller sub-container units,
a sub-container is a standardized, modular unit design to fit securely inside a standard shipping container with little space left over,
a sub-container is a re-usable, durable shipping enclosure that is packaged for specific destinations,
sub-containers are transferred to an underground automated freight system which conveys the smaller containers from the factory ring to the underground loading dock of each of the buildings within the cluster city, eliminating the need for freight trucks and roads,
newly loaded freight cars connect to an outside main line delivery track connected to an open-loop track entrance and exit system rail lines,
(n) a plurality of wi-fi hotspots occur within the new buildings at all floors, with a multitude of signals being issued in controlled distance that provide two way talk, information dissemination, internet access, location generation,
(o) security control of communications by limiting distances of the signals to within the building and others that will reach to all the other buildings within the cluster city
(p) the new building structures allow design and installation of automated building technologies that are created for digital response,
(q) new buildings allow full integration of food and waste conveyance systems connecting underground to the vertical farm facility to convey waste and receive food,
(r) new buildings allow for the automated freight system to connect underground from the factory ring to each cluster city building.

2. An ecological, sustainable and high performance city system, as described in claim 1, wherein the city system is configured to protect human health and improve sustainability of the inhabitants by employing a plurality of nodal locations of life-sustaining buildings whose technologies are comprised as follows:
(a) all buildings within the cluster city are equipped with a new environment created to protect human health from the effects of extreme climate change which is configured in the following ways, a controlled indoor air quality system which purifies the air to protect the inhabitants from breathing pollution causing chronic lung and chronic cardiovascular diseases, a controlled indoor air quality system with temperature control to eliminate temperature-related death and illness, a controlled indoor air quality system which prevents introduction of vector-borne diseases carried by mosquitoes, ticks and fleas by creating various insect barriers at all building entrances, a water recycling system providing occupants with purified and recycled water which prevents occupants from imbibing harmful contaminants found in groundwater, a vertical farm food production system on-site which produces safe, sanitary food with high nutritional level with constant supply that replaces imported food which is susceptible to supply variations due to climate change; insect and disease predation; and potential toxic chemical exposure, a safe, on-site, non-polluting energy facility which produces a consistent a supply of all power requirements for people, buildings, transportation and industry without emitting greenhouse gases and other noxious particles, buildings are all designed to protect their inhabitants from attacks of both natural disaster and man-made disasters or attacks, this protects people from both physical and mental stress-inducing events, (b) all buildings within the cluster city are equipped with a closed air system protecting inhabitants from illness caused by breathing polluted air, remedied with a system that re-circulates interior air comprised of the following technology:

an air scrubbers/purifiers apparatus for removal of expelled CO2 gas, an heating and cooling apparatus to stabilize temperature changes, an air blower apparatus to instill air movement, a dehumidifying apparatus to absorb moisture from expelled breathing, an oxygen injecting apparatus to supplement low atmospheric levels oxygen a particulate filtering apparatus straining air to 0.01 microns to prevent introduction and sustained presence of bacteria, molds, insects, pollen and fine particulate chemicals from outside, an ultra violet light sterilizers embedded in air ducts to kill viruses that cannot be strained out, an air compressor to capture expelled air and exhaust it to the plant growth chambers in the vertical farms to be exchanged with oxygenated air charged by plants, (c) all buildings within the cluster city maintain a net-zero water system supply which is independent from groundwater sourcing comprised of, a plurality of water systems, one for drinking, one for bathing and a third for flushing toilets with each system operating to a specific level of purity, a filtering apparatus uses reverse osmosis filtration, combined with ultra-violet purification lamps to produce drinking water eliminating human imbibing of microbes, toxic metals and toxic viruses, a sand filtering apparatus for changing gray-water into bath water also by adding a sterilizer, a containment vessel coagulates black water and flocculates it to remove all sewage waste, sewage waste is conveyed to the recycling plant at the vertical food production facility, additional treatment of waste water from the factories may include dissolved chemicals which needs separate from generalized decomposition, rainwater is harvested from all building surfaces, purified then distributed for drinking, each building has underground cisterns of 4-10 million gallons for water supply and geothermal heat storage, each building has a constant water supply regardless of how scarce external water resources;

(d) clean food is produced 24 hours per day, 365 days per year from the on-site vertical farm food production facility, this curving, concrete "donut-shaped" building is comprised of:

a plurality of concrete floors separated by masonry walls to define a variety of airtight growth chambers, an airtight growth chambers shall maintain positive air pressure to prevent incoming air to carry contaminants, a plurality of elevators to transfer goods between floors, each growth chamber has HVAC systems with temperature controls for leaf tissue growth wind speed is controlled by a plurality of fans in each growth chamber to optimize transpiration and tissue growth, air is re-circulated and monitored for adjustment of CO2 levels to maximize growth, humidity levels is controlled in each growth chamber for optimal plant growth, water is recycled and filtered with dehumidified condensates from plant transpiration, then added back into solution that goes to the nutrient solution, minimizing the net amount of water needed for each plant, non-absorbed nutrients from used solution will be recycled into fresh solutions, a liquid nutrient systems has control of temperature, flow rate, aeration and Ph sensors for each growth chamber, a digitally controlled lighting system changes light color, saturation levels, brilliance and duration for each growth chamber, a plurality of support racks to hold plants into a vertical plane growth system for each growth chamber, a plurality of chutes and conveyors to transfer food downstairs, a plurality of food preparation rooms where harvested food is trimmed and boxed for conveyance, a conveyance system to transfer boxed food from the vertical farm facility to each of the buildings where food is consumed, a computer control center that receives digital input of sensor monitors from each growth chamber, a clean room where workers bathe and change into clean work clothes for work inside each growth chamber, a pressurized air system creating positive pressure at all building exits, an input duct from outside buildings feeding CO2 expelled air from occupied buildings into the growth chambers of the vertical farm to enhance photosynthesis, food produced inside the growth chambers employs either hydroponic or aeroponic techniques depending on which plant is involved, a plurality of water-filled tanks containing aquaponically produced fish occupy other growth chambers, a plurality of water-filled tanks containing aquaponically produced algae occupy other growth chambers, a majority of nutrients for the food production come from processed recycled waste from the occupied buildings by means of a pumped slurry system, the on-site power system generates electricity for the lighting, heat, cooling, pumps and monitors used in the vertical farm facility, a plurality of solar panels occur on the roof to convert solar energy into electricity, a water catchment system on the roof will harvest rainwater, where it is filtered, purified and distributed downstairs and also to other occupied buildings, the Vertical Farm Facility produces over 90% of the cluster city food requirements on-site with the remainder produced on-site in permanent orchards within cloistered compounds or imported in trade, (e) a clean energy system provides electricity and industrial heat is produced with base-load power by a series of small modular reactors with generation iv advanced technology and supplemented by renewable energy sources within in a local micro-grid system, comprised as follows, the reactors use a power-source comprised of either uranium and/or thorium utilizing a heat exchange medium of liquid sodium or liquid lead or helium gas which converts nuclear fission heat energy into steam vapor driving a gas turbine electrical generator, the reactors occur in smaller units that merge together to produce all the required energy, their individual output can increase to compensate for one or two units that are non-functional for repair, replacement of fissile material or reinvigorating such fuel for greater efficiency, renewable energy from solar and wind sources supplement the nuclear base-load power generation located on the roof of the factory ring, the vertical farm building and the top of the layered transportation corridor, energy from local nuclear reactors are used to convert water into hydrogen and oxygen using an electrolysis generator thus providing hydrogen as a clean burning mobile energy source for fuel cells and oxygen for breathing supplementation in buildings, excess heat from the reactors is diverted into auxiliary co-generation units to produce additional electricity and reduce heat instead of using water from rivers, lakes and oceans for cooling, excess energy generated by renewable sources that is not consumed immediately within the system, will be stored in an energy storage chamber comprised of one of the following energy storage mediums; molten salt, lithium, super-capacitor, flow battery, centrifugal spinning weight or hydrogen conversion with compressed storage, renewable energy is integrated with nuclear by use of digital control system that reduces the fission load while increasing the renewable load of wind and solar output, the zero greenhouse gas emission power generation is used for all the buildings, transportation systems and vertical farm facility of the city system with no outside interference from natural and man-made disasters, the heat generated in the nuclear reactors is used to enable industrial production of glass, cement, steel and aluminum fabrication thus eliminating the use of electric arc and forced-air carbonaceous fossil fuels to achieve desired heat levels, heat from local nuclear reactors is used to make distilled water from ocean water to supplement the net-zero water system in the buildings, the micro-grid system is used for short distance power to the end user and is much more efficient with virtually no power loss in long-distance transmission currently incurred with grid power system, the micro-grid is not susceptible to cyber-attack or grid cascade failure with localized control within the network firewall, whereas the current large-scale grid power system is vulnerable to attack along the entire network with any digital network entrance allowing outside control or manipulation, trunk lines of electricity power are transferred by very thick cable in underground services tunnels exclusively from one building to another to eliminate cable damage during windstorms an energy storage system is present in each building to allow for emergency continuity in case of power interruption all components of the energy system will be housed underground with access only from secured tunnels;

(f) improved building designs and fabrication are the key factors to sustainability with these fortress-like features;

all building are engineered for high-winds up to 400 mph with possible cyclonic uplift and reinforced corners using curved surfaces to reduce wind resistance, hot and cold temperature extreme of −80 C to +50 C are nullified with new insulated foams, use of double and triple pane glass windows with high impact outer pane preventing direct damage and insulates against heat and cold; building infrastructure is equipped with the most current energy efficient devices, such as electrical motors, lighting, heating, air conditioning, water pumps, elevators, escalators, kitchen equipment and other equipment used in building operations, all buildings are located in the proper place to prevent flooding with the ground floor level significantly above historical flood plain levels and use of water-proof sealants applied to all exposed joints where leakage may occur, all building structures and foundations are fabricated to mitigate seismic events up to a Richter Scale level 10.0, all buildings have mega-structure building structural foundations designed to integrate vertical and seismic loading to reduce seismic movement and uneven weight distribution during earthquake events with designs for both single monolithic towers or multi-tower configurations (g) all buildings have a limited number of entry points with screening of people and positive air pressure stopping microbial and insect entry to prevent unwanted entry of people, diseases and other species, (h) security cameras are positioned throughout each building using facial recognition measures insure that any criminal incident is observed and identified, children can move freely without an escort, as they are watched by cameras (i) open space between buildings isolates and reduces crime within a localized population (j) elevated mass-transit is enclosed with sides screens while the autonomous vehicle taxi level is roofed with side screens to prevent extreme weather anomalies from causing accidents with lateral winds blowing snow hail and rain on the surface; both transportations systems have self-contained controlled environments on-board to protect from air pollutants, reducing stress while increasing safety, (k) all high-speed elevators shall all employ automatic self-braking mechanisms to prevent injury from free-fall, (l) terrorist attacks are resisted with proper building structure incorporations, (m) resiliency plans are in place to react to all emergencies; including building repair from high-impacts and wind shear.

3. An ecological, sustainable and high performance city system as described in the Cluster City of claim 2, the method to mitigate ecological disruption caused from human activities by employing adaptation practices that diminish increases in ecological entropy comprised as follows:

(a) human disruption of environmental harmony in existing sprawl cities is corrected by the following activities:

on-site nuclear and renewable clean-energy equipment creating zero greenhouse gases emissions into the atmosphere reducing climate change disruption, restricting the use of chlorine and fluorine gases that disrupt the stratosphere boundary layer creating holes which cause vertical storms and ozone holes, no on-site ruminant food production while internalizing rice production hydroponically in the vertical farm to eliminate release of methane gas from paddy fields, vertical farm food production allows hundreds of varieties of food to be grown due to the great diversity of seed, environment and nutrient combinations eliminating the need to provide food for inhabitants that comes from only a few varieties of food animals en mass, causing a loss of biodiversity of thousands of birds and animals, outside agriculture results in plowing the soil that caused dehydration and loss of vitality, loss of top soil to wind and water erosion, adding chemicals in the soil that leach into the groundwater, adding ground water with dissolved solids into the soil, systematic elimination of solid waste food packaging is achieved by employing re-usable and recyclable containers, eliminating individual kitchens in residence by having food courts, restaurants and delivery to habitations, all paper, wood, plastic, glass, metals and chemicals will all be recycled or incinerated to eliminate disposal into landfills that consume space that could otherwise be returned to wilderness, total sewage waste decomposition, mostly organics, is recycled completely beneath the vertical farm food production center accomplished with the correct, heat, grinding and stirring with algae that returns it to pure nutrient matter with no release methane gas to disrupt the atmosphere;

the aquaponics in growth chambers of vertical farm produces clean, nutritious fish without contaminants thus retarding over-fishing the oceans, lakes and rivers by offering a healthier choice, industries within the cluster city do not release acids, chemicals and floating plastics that end up contaminating the oceans, a one-baby rule within the cluster city reducing human overpopulation that causes excessive orientation of nature to the human species (intensifying entropy) with decline of other species (extinction), personal storage space and cost of consumption taxes in the cluster city reduce personal consumption of goods;

(b) Retractive Development—The only form of city development that is truly sustainable and not destructive to the environment, it improves the ecological balance (reduction of entropy through neg-entropic means) of the habitat in the following ways:

human activity is restricted to vertical development, instead of horizontal surface sprawl, so the majority of land surface may be restored into urban forests with no human structures present, urban forests are created in the open space between micro-cities that act as a wildlife habitat for increased biodiversity of plants and animals, urban forests are created in the open space between the vertical farm facility and the micro-cities for increased biodiversity of plants and animals, urban forests are created in the open space between the factory ring facility and the micro-cities for increased biodiversity of plants and animals, urban forests are created in the open space between the layered transportation corridors and the micro-cities for increased biodiversity of plants and animals, the layered transportation corridors maintain an open passageway tunnels at ground level so that animals can penetrate the entire city one segment to another using these egress tunnels, urban forests between buildings reduce heat island effects by absorbing solar energy; whereas sprawling cities have solid buildings, roads and parking lots creating heat from solar absorption on hard surfaces, urban forests act as a carbon sink to purify the air of CO2, urban forests create a permanent non-tillage zone for soils to restructure allowing a plurality of microorganisms to reside there, urban forests with non-tilled soils allow floodwaters to percolate downward preventing inter spatial water buildup, urban forests contain lakes, ponds and streams to act as heats flow buffers allowing more surface air flow;

urban forests buffer and prevent pandemic disease transmission by increasing biodiversity, (c) on-site food production with the vertical farm facility allows unproductive land outside the city system to be restored to wilderness condition comprising the following mitigating techniques:

the soil micro-biome is restored to an undisturbed condition from repeated tilling activities allowing micro life to flourish and rebuild, chemical fertilizer damage to micro life is mitigated through natural rain flushing rainwater flushing of damaged soil mitigates dissolved solids that build up in the soil resulting from groundwater irrigation, cessation of farm equipment operations mitigates release greenhouse gases, (d) on-site food production within the confines of the vertical farm facility comprises the following restorative measures:

a water-based hydroponic nutrient medium replaces the use of soil, mechanically and chemically eliminating damage to outside soil life from tillage, a self-contained, recycling nutrient system prevents chemical discharge into the soil, the water cycle is isolated by nutrient recycling with filtration, plus plant transpiration water being recycled with dehumidifier to eliminate need for groundwater extraction, rainwater catchment from the vertical farm roof is filtered then injected into nutrient solution as needed for each plant type, an underground conveyor food delivery from on-site food production to all buildings reduces energy usage to transport food into city from trucking, indoor factory food production reduces energy use compared to large diesel farm machines traversing the fields to create the same crop operations, indoor food production using non-greenhouse gas electricity produces no release of greenhouse gases into the atmosphere compared to farm machinery utilizing fossil fuel power, on-site food production use of re-usable shipping containers reduces solid waste compared to single-use corrugated boxes, all operations within the vertical farm facility are powered by non-fossil fuels having a net-zero co2 emission footprint, (e) all electric transportation system comprised of elevators, mass transit trains, buses and autonomous vehicles eliminates the use of cars and trucks with their fossil fuel based power requirements, (f) recycling waste in the underground area of the vertical farm facility eliminates landfill methane generation and release damaging the atmosphere, (g) overall reduction of city system ecological footprint (human demand on nature) to 0.5 per person (global hectares) compared to full natural solar rejuvenation of 1.0 provides natural space for other species to co-habit the earth and typical sprawl cities averaging about 6.0 hectares per person.

4. An ecological, sustainable and high performance city system, as described in claim 2, the system is configured to improve safety and survivability to occupants while moving from one building to another during disruptive climate events, these physical improvements comprise the following:

(a) a transportation corridor connecting movement from one cluster city building to another that provides the following elements:

lower levels are built to withstand ground level flooding water intrusion, a plurality of high-impact windows built to withstand wind and debris collisions, a sealed and controlled environment inside with heating and cooling mechanisms that protects occupants against temperature extremes of heat and cold, multi-layered with sealed controlled environment for pedestrian and human powered movement so occupants will not breathe polluted air, built to protect against air pollution and toxicity with filtration systems, CO2 scrubbers and oxygen supplementation, as needed, waterproof seals that prevent water penetration at doors and windows from water penetration so occupants will not get wet, (b) the transportation corridors connecting movement from one cluster city building to another that provide layers for mass-transit and autonomous vehicles with side-panel wind screens to prevent wind, snow and debris in contact with the vehicles, (c) these corridors are stacked in vertical traffic layers, thus reducing the horizontal footprint so that land can be returned to urban forests, (d) building portals that interface the transportation corridor to a building that comprise the following:

a roof canopy extending from the side of the building outward, 4 lanes or 35 feet wide minimum, with a solid wall on the far side, for the entrance and exit from the corridor, has air-wall blowers that seal the canopy from exterior air intrusion so that vehicles may pass without physical restriction while maintaining the controlled environment, a plurality of connection joints that are impact resistant from wind or water driven debris, a controlled environment connection that seals against loss of air quality from leakage to the outside in the pedestrian and human powered layers, a multi-level apparatus that connects of the transportation corridor to the building, portals for masstransit and autonomous vehicle taxis that provide wind screens and semi-controlled environments for passengers to disembark vehicles to enter buildings, (e) the transportation corridor system for the cluster city provides continuous, safe egress from one building to another building without any disruption caused by inclement or extreme weather conditions.

5. An ecological, sustainable and high performance city system, as described in claim 3, the system is configured to improve efficiency of operation of a smaller city comprised of:

(a) a medium-sized, medium density, smaller cluster city with population design for 50,000 to 1,000,000 inhabitants, (b) a compact, walk able, transit oriented mixed-use city that eliminates cars, trucks and roads, (c) a plurality of concentrically arranged micro-city buildings for concentrated human living with over 4,000 people per square kilometer and surrounding the central city core, (d) a small cluster city arrangement that may vary depending on population size and function of the city system, (e) a micro-city building larger than 800,000 sq. feet area that comprises residential living, as well as typical mixed-use activities while eliminating the use of cars and trucks, (f) a plurality of specialty cities that combine the following unique individual functions:

government building with shopping galleria,
undergrad and post-graduate university,
performing arts with sports/recreation and museums,
hospital with senior care center, (e) a series of transit station to station orientated buildings insuring a simplified system with people traveling to their destinations faster with less walking; and without weather inconveniences by never leaving controlled environment transportation corridors, (f) a two-way mass transit, both concentrically and radially, allowing for large movement of people from one micro-city transit station to the next within the framework of a smaller compact city, (g) a smaller factory ring is used to:
provide a controlled environment domains for work,
provide space for unloading and loading of freight train container cars at ground level, provide space to repackage goods into sub-containers that travel underground to the automated freight handling system for distribution to each building's distribution warehouse, (h) a smaller vertical farm food production center with a,
a smaller circular ring sized to feed a lesser population with a similar above ground facility,
a smaller waste conversion system below ground facility interacting with less buildings, (i) a series of small modular, advanced design nuclear reactors that operate together to yield a variety of power levels depending upon demand requirements, with power distribution of a local micro-grid delivery system for a single smaller cluster city having zero greenhouse gas emission, (j) A new building fortress design that structurally protects people from the effects of extreme climate change.

6. An ecological, sustainable and high performance city system, where the system is configured as a regional land arrangement comprised of:

(a) a plurality of cluster cities organized in proximate vicinity, connected to interact as a singular socio/economic mega-city regional center, (b) a plurality cluster cities are each designated as a specialized city functioning as:
a main capital city regional seat of government for the executive, council of representatives from each cluster city and a judicial branch,
a main financial center where all intercity financial activities are focused
a main communications center being connected by various intercity communication systems comprised of:
5G digital signals
banking system signals
security system signals
energy distribution signals
fiber optic trunk lines
all linkages between cluster cities shall be based on "cloud technology" firewalls with individual isolation to prevent cyber-attack internally
a main entertainment/amusement/performing arts center where visitation occurs mostly for enjoyment,
a main sporting center having activities not found in individual cluster cities and includes a large 100,000 person sports event arena
a regional hospital center has health specialists in all disciplines and has a roof-top mede-vac station to receive patients from adjacent cluster cities for emergency care and transport to the regional airport,
a regional university center where the highest level of graduate education and research occurs
a regional museum and zoological center where the great ancient cultural treasures of art, artifacts and animals occurs (c) a transportation hub cluster city that acts as:
a distribution point along the oval shaped-closed circuit connecting each cluster city central transportation hub to this regional mega-city using regional two-way transportation corridors,
a distribution point of a bi-level two-way corridor cross-over link that connects with a cluster city on the far side of the loop to the transportation hub and then continues on to the regional airport connecting,
a distribution point to transfer from the regional transportation corridor to the main national high-speed train system that travels to other regional mega-city locations (d) a regional transportation corridor system comprised of:
a regional two-way, closed loop transportation corridor structure that allows rapid movement of people from any cluster city to another or to the regional airport,
a high-speed train such as magnetic-levitation or other such fast-acceleration electric trains capable of connecting cluster city central transportation hubs to each other within 10 minutes, occurring at either ground level or underground
an elevated autonomous vehicle taxi level, above the high-speed train level, which is capable of high-speed travel for movement to any of the cluster cities or being transferred at the regional transportation hub for connection to the regional airport,
a two-way train and autonomous vehicles bi-level corridor connecting with the regional airport about 10-20 miles distance to the regional transportation hub,
a two-way corridor link between opposite cluster cities on the oval-shaped loop,
a linear structure that has protective side screens to prevent wind-carried debris, snow, hail and ice from contacting the train-tracks and top level roadway,
a linear structure that has a protective roof preventing snow, wind, hail and debris from contacting the top roadway;

(e) a freight hub cluster city is comprised of:
one or two designated freight hubs handling freight train distribution, one hub for each of the two-way main national train lines passing through the regional mega-city regional center
a large train switch yard where incoming and outgoing containers are hoisted on-board flat cars for on-going movement either inbound to the individual cluster city arrangement or outbound to other regional centers,
the freight hub utilizes lifting cranes to move containers from self motive carriages within the cluster city to flatbed cars to are interconnected to be a part of commercial trans-national freight train,
a freight switch yard is part of the outer perimeter of one side of a designated transportation hub cluster city and has an area for parking tracks, loading and driving lanes, as well as handling trans-shipments of freight trains, (f) a zero greenhouse gas emission mega-city energy system comprised of:
a series of small modular, advanced design nuclear reactors operating together to yield a variety of power levels depending upon demand requirements, with power distribution of a local micro-grid delivery system for a single smaller cluster city,
all independent cluster city energy systems have outbound connectivity called a supra-grid system that allow for energy sharing within the mega-city, used in case there is an emergency, periodic maintenance or replacement.

\* \* \* \* \*